US008512695B2

(12) United States Patent
Austen, Jr.

(10) Patent No.: US 8,512,695 B2
(45) Date of Patent: Aug. 20, 2013

(54) METHOD OF PREVENTING FAT GRAFT RESORPTION BY ADMINISTERING FAT-DERIVED CELLS AND POLOXAMER P 188

(75) Inventor: William G. Austen, Jr., Weston, MA (US)

(73) Assignee: The General Hospital Corporation, Boston, MA (US)

( * ) Notice: Subject to any disclaimer, the term of this patent is extended or adjusted under 35 U.S.C. 154(b) by 783 days.

(21) Appl. No.: 12/603,075

(22) Filed: Oct. 21, 2009

(65) Prior Publication Data

US 2010/0104542 A1    Apr. 29, 2010

Related U.S. Application Data

(60) Provisional application No. 61/107,023, filed on Oct. 21, 2008.

(51) Int. Cl.
| A01N 63/00 | (2006.01) |
| A61F 2/00 | (2006.01) |
| C12N 5/00 | (2006.01) |
| C12N 5/07 | (2010.01) |

(52) U.S. Cl.
USPC .......................... 424/93.7; 424/423; 435/325

(58) Field of Classification Search
None
See application file for complete search history.

(56) References Cited

U.S. PATENT DOCUMENTS

| 5,052,999 | A | 10/1991 | Klein |
| 5,212,071 | A | 5/1993 | Fearon et al. |
| 5,256,642 | A | 10/1993 | Fearon et al. |
| 5,470,568 | A | 11/1995 | Lee |
| 5,472,939 | A | 12/1995 | Fearon et al. |
| 5,489,694 | A | 2/1996 | Paust et al. |
| 5,569,670 | A | 10/1996 | Weischer et al. |
| 5,605,687 | A | 2/1997 | Lee |
| 5,621,117 | A | 4/1997 | Bethge et al. |
| 5,650,428 | A | 7/1997 | Ohmori et al. |
| 5,681,561 | A | 10/1997 | Hirshowitz et al. |
| 5,693,664 | A | 12/1997 | Wessel et al. |
| 5,709,868 | A | 1/1998 | Perricone |
| 5,716,404 | A * | 2/1998 | Vacanti et al. ..................... 623/8 |
| 5,728,735 | A | 3/1998 | Ulrich et al. |
| 5,856,297 | A | 1/1999 | Fearon et al. |
| 5,965,618 | A | 10/1999 | Perricone |
| 5,981,481 | A | 11/1999 | Fearon et al. |
| 6,090,842 | A | 7/2000 | Packer et al. |
| 6,103,255 | A | 8/2000 | Levene et al. |
| 6,277,842 | B1 * | 8/2001 | Carthron ........................ 514/188 |
| 6,316,604 | B1 | 11/2001 | Fearon et al. |
| 6,331,559 | B1 | 12/2001 | Bingham et al. |
| 6,353,011 | B1 | 3/2002 | Pershadsingh et al. |
| 6,359,014 | B1 | 3/2002 | Emanuele et al. |
| 6,365,623 | B1 | 4/2002 | Perricone |
| 6,605,637 | B1 | 8/2003 | Harnett et al. |
| 6,696,575 | B2 | 2/2004 | Schmidt et al. |
| 7,202,056 | B2 | 4/2007 | Lee et al. |
| 7,220,557 | B2 | 5/2007 | Iruela-Arispe et al. |
| 7,227,007 | B2 | 6/2007 | Matsuda et al. |
| 7,390,484 | B2 | 6/2008 | Fraser et al. |
| 7,482,152 | B2 | 1/2009 | Ramasubramanian |
| 7,588,732 | B2 | 9/2009 | Buss |
| 7,700,086 | B2 * | 4/2010 | Schwarz ..................... 424/78.08 |
| 7,723,085 | B2 * | 5/2010 | Smith et al. ................... 435/177 |
| 7,824,847 | B2 | 11/2010 | Steinhardt |
| 8,067,359 | B2 * | 11/2011 | Hayes et al. .................... 514/1.1 |
| 8,071,085 | B2 * | 12/2011 | Ito et al. ...................... 424/93.21 |
| 2002/0012642 | A1 | 1/2002 | Perricone |
| 2002/0016570 | A1 | 2/2002 | Cartledge |
| 2002/0042372 | A1 | 4/2002 | Olsen et al. |
| 2003/0054374 | A1 | 3/2003 | Ramanathan et al. |
| 2003/0092017 | A1 | 5/2003 | Finger et al. |
| 2003/0092900 | A1 | 5/2003 | Iruela-Arispe et al. |
| 2003/0118545 | A1 | 6/2003 | Shi et al. |
| 2003/0162189 | A1 | 8/2003 | Lee et al. |
| 2003/0180337 | A1 | 9/2003 | Streicher et al. |
| 2003/0224450 | A1 | 12/2003 | Lee et al. |
| 2003/0224486 | A1 | 12/2003 | Carman et al. |
| 2004/0002449 | A1 | 1/2004 | Iruela-Arispe et al. |
| 2004/0002509 | A1 | 1/2004 | Adams et al. |
| 2004/0018976 | A1 | 1/2004 | Feder et al. |

(Continued)

FOREIGN PATENT DOCUMENTS

| EP | 0 427 247 A2 | 5/1991 |
| WO | WO 89/09220 A1 | 10/1989 |

(Continued)

OTHER PUBLICATIONS

Vashi et al., Adipose differentiation of bone marrow-derived mesenchymal stem cells using Pluronic F-127 hydrogel in vitro. Biomaterials. Feb. 2008;29(5):573-9. Epub Nov. 5, 2007.
Agarwal et al., Multimodal strategies for resuscitating injured cells. Ann N Y Acad Sci. Dec. 2005;1066:295-309.
Baczkó et al., Pharmacological activation of plasma-membrane KATP channels reduces reoxygenation-induced Ca(2+) overload in cardiac myocytes via modulation of the diastolic membrane potential. Br J Pharmacol. Mar. 2004;141(6):1059-67. Epub Mar. 1, 2004.
Boodhwani et al., Effects of purified poloxamer 407 gel on vascular occlusion and the coronary endothelium. Eur J Cardiothorac Surg. May 2006;29(5):736-41. Epub Apr. 12, 2006.
Cadichon et al., Neuroprotective effect of the surfactant poloxamer 188 in a model of intracranial hemorrhage in rats. J Neurosurg. Jan. 2007;106(1 Suppl):36-40.

(Continued)

*Primary Examiner* — David M Naff
(74) *Attorney, Agent, or Firm* — Wolf, Greenfield & Sacks, P.C.; C. Hunter Baker

(57) ABSTRACT

The present invention provides polymers for use in preventing damage to the membranes of cells in fat grafts. Mixing of a triblock copolymer such as poloxymer P188 with adipocytes or adipose tissue to be transplanted into a subject is thought to stabilize the membranes of the cells leading to more successful fat transplantation in soft tissue reconstruction or augmentation. Such methods may also be used in the transplantation of adult stem cells or other cells derived from fat tissue. Other agents such as lipoic acid may also be added to the polymer/cell compositions for cell transplantation.

14 Claims, 14 Drawing Sheets

(56) References Cited

U.S. PATENT DOCUMENTS

| | | | |
|---|---|---|---|
| 2004/0025195 A1 | 2/2004 | Lee et al. | |
| 2004/0030098 A1 | 2/2004 | Lee et al. | |
| 2004/0081986 A1 | 4/2004 | Matsuda et al. | |
| 2004/0086896 A1 | 5/2004 | Carman et al. | |
| 2004/0087543 A1 | 5/2004 | Shriver et al. | |
| 2004/0116350 A1 | 6/2004 | Wentworth, Jr. et al. | |
| 2004/0198658 A1 | 10/2004 | Olsen et al. | |
| 2004/0204576 A1 | 10/2004 | Jackson et al. | |
| 2004/0265345 A1 | 12/2004 | Perricone | |
| 2004/0265388 A1 | 12/2004 | Zhang et al. | |
| 2005/0069520 A1 | 3/2005 | Shi et al. | |
| 2005/0084961 A1 | 4/2005 | Hedrick et al. | |
| 2005/0118632 A1 | 6/2005 | Chen et al. | |
| 2005/0158358 A1 | 7/2005 | West et al. | |
| 2005/0175665 A1* | 8/2005 | Hunter et al. | 424/423 |
| 2006/0121016 A1 | 6/2006 | Lee et al. | |
| 2006/0182725 A1* | 8/2006 | Marko et al. | 424/93.7 |
| 2006/0184101 A1 | 8/2006 | Srinivasan et al. | |
| 2007/0071743 A1 | 3/2007 | Lee et al. | |
| 2007/0110731 A1 | 5/2007 | Riley | |
| 2007/0237740 A1 | 10/2007 | Reddington et al. | |
| 2009/0017438 A1 | 1/2009 | Roy et al. | |
| 2009/0017439 A1 | 1/2009 | Shimko et al. | |
| 2009/0239299 A1 | 9/2009 | Buss | |
| 2012/0128641 A1 | 5/2012 | Austen, Jr. | |

FOREIGN PATENT DOCUMENTS

| | | |
|---|---|---|
| WO | WO 91/05047 A1 | 4/1991 |
| WO | WO 93/15745 A1 | 8/1993 |
| WO | WO 99/61440 A1 | 12/1999 |
| WO | WO 00/50639 A2 | 8/2000 |
| WO | WO 01/30969 A2 | 5/2001 |
| WO | WO 02/16557 A2 | 2/2002 |
| WO | WO 02/072755 A2 | 9/2002 |
| WO | WO 02/077173 A2 | 10/2002 |
| WO | WO 02/086076 A2 | 10/2002 |
| WO | WO 02/092107 A1 | 11/2002 |
| WO | WO 03/012063 A2 | 2/2003 |
| WO | WO 03/083078 A2 | 10/2003 |
| WO | WO 2004/039940 A2 | 5/2004 |
| WO | WO 2004/048529 A2 | 6/2004 |
| WO | WO 2004/094621 A2 | 11/2004 |
| WO | WO 2004/100886 A2 | 11/2004 |
| WO | WO 2005/072343 A2 | 8/2005 |
| WO | WO 2006/037031 A2 | 4/2006 |
| WO | WO 2006/044738 A2 | 4/2006 |
| WO | WO 2007/005668 A2 | 1/2007 |
| WO | WO 2010/047793 A2 | 4/2010 |
| WO | WO 2011/059733 A2 | 5/2011 |
| WO | WO 2012/019103 A2 | 2/2012 |

OTHER PUBLICATIONS

Coleman, Structural fat grafts: the ideal filler? Clin Plast Surg. Jan. 2001;28(1):111-9.

Curry et al., Poloxamer 188 volumetrically decreases neuronal loss in the rat in a time-dependent manner. Neurosurgery. Oct. 2004;55(4):943-8; discussion 948-9.

Forman et al., Role of perfluorochemical emulsions in the treatment of myocardial reperfusion injury. Am Heart J. Nov. 1992;124(5):1347-57.

Gimble et al., Adipose-derived stem cells for regenerative medicine. Circ Res. May 11, 2007;100(9):1249-60.

Gutkowski, Current applications and safety of autologous fat grafts: a report of the ASPS fat graft task force. Plast Reconstr Surg. Jul. 2009;124(1):272-80.

Hannig et al., Surfactant sealing of membranes permeabilized by ionizing radiation. Radiat Res. Aug. 2000;154(2):171-7.

Justicz et al., Reduction of myocardial infarct size by poloxamer 188 and mannitol in a canine model. Am Heart J. Sep. 1991;122(3 Pt 1):671-80.

Kelly et al., Effect of Poloxamer 188 on Collateral Blood Flow, Myocardial Infarct Size, and Left Ventricular Function in a Canine Model of Prolonged (3-Hour) Coronary Occlusion and Reperfusion. J Thromb Thrombolysis. Jul. 1998;5(3):239-247.

Kolodgie et al., Hyperoxic reperfusion is required to reduce infarct size after intravenous therapy with perfluorochemical (Fluosol-DA 20%) or its detergent component (poloxamer 188) in a poorly collateralized animal model. Absence of a role of polymorphonuclear leukocytes. J Am Coll Cardiol. Oct. 1994;24(4):1098-108.

Lee et al., Surfactant-induced sealing of electropermeabilized skeletal muscle membranes in vivo. Proc Natl Acad Sci U S A. May 15, 1992;89(10):4524-8.

Lee et al., Direct observation of the p188 mediated membrane sealing with atomic force microscopy. MCB. 2006;3(4):185-6.

Marks et al., Amphiphilic, tri-block copolymers provide potent membrane-targeted neuroprotection. FASEB J. Apr. 2001;15(6):1107-9.

Maskarinec et al., Direct observation of poloxamer 188 insertion into lipid monolayers. Biophys J. Mar. 2002;82(3):1453-9.

Maskarinec et al., Membrane sealing by polymers. Ann N Y Acad Sci. Dec. 2005;1066:310-20.

Maynard et al., Randomized, controlled trial of RheothRx (poloxamer 188) in patients with suspected acute myocardial infarction. RheothRx in Myocardial Infarction Study Group. Am Heart J. May 1998;135(5 Pt 1):797-804.

Mina et al., Poloxamer 188 copolymer membrane sealant rescues toxicity of amyloid oligomers in vitro. J Mol Biol. Aug. 21, 2009;391(3):577-85. Epub Jun. 12, 2009.

O'Keefe et al., Poloxamer-188 as an adjunct to primary percutaneous transluminal coronary angioplasty for acute myocardial infarction. Am J Cardiol. Oct. 1, 1996;78(7):747-50.

Quinn et al., Adjunctive use of the non-ionic surfactant Poloxamer 188 improves fetal dopaminergic cell survival and reinnervation in a neural transplantation strategy for Parkinson's disease. Eur J Neurosci. Jan. 2008;27(1):43-52. Epub Dec. 15, 2007.

Schaer et al., Reduction in reperfusion-induced myocardial necrosis in dogs by RheothRx injection (poloxamer 188 N.F.), a hemorheological agent that alters neutrophil function. Circulation. Dec. 1994;90(6):2964-75.

Schaer et al., Beneficial effects of RheothRx injection in patients receiving thrombolytic therapy for acute myocardial infarction. Results of a randomized, double-blind, placebo-controlled trial. Circulation. Aug. 1, 1996;94(3):298-307.

Serbest et al., Mechanisms of cell death and neuroprotection by poloxamer 188 after mechanical trauma. FASEB J. Feb. 2006;20(2):308-10. Epub Dec. 21, 2005.

Serbest et al., The effect of poloxamer-188 on neuronal cell recovery from mechanical injury. J Neurotrauma. Jan. 2005;22(1):119-32.

Singh-Joy et al., Safety assessment of poloxamers 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and 407, poloxamer 105 benzoate, and poloxamer 182 dibenzoate as used in cosmetics. Int J Toxicol. 2008;27 Suppl 2:93-128.

Watanabe et al., Lysophosphatidylcholine-induced myocardial damage is inhibited by pretreatment with poloxamer 188 in isolated rat heart. Mol Cell Biochem. Jun. 2003;248(1-2):209-15.

Wu et al., Interaction between lipid monolayers and poloxamer 188: an X-ray reflectivity and diffraction study. Biophys J. Nov. 2005;89(5):3159-73. Epub Aug. 12, 2005.

Zhang et al., Effect of Pluronic F-68 on the mechanical properties of mammalian cells. Enzyme Microb Technol. Dec. 1992;14(12):980-3.

International Preliminary Report on Patentability for PCT/US2009/005727, mailed May 5, 2011.

International Search Report and Written Opinion for PCT/US2010/002033, mailed Apr. 28, 2011.

International Preliminary Report on Patentability for PCT/US2010/002033, mailed Feb. 2, 2012.

International Search Report and Written Opinion for PCT/US2010/054451, mailed Jul. 20, 2011.

International Preliminary Report on Patentability for PCT/US2010/054451, mailed May 10, 2012.

Invitation to Pay Additional Fees for PCT/US2011/046752, mailed Nov. 29, 2011.

International Search Report and Written Opinion for PCT/US2011/046752, mailed Feb. 23, 2012.

Al-Rubeai et al., Cell cycle and cell size dependence of susceptibility to hydrodynamic forces. Biotechnol Bioeng. Apr. 5, 1995;46(1):88-92.

Anthony et al., Pluronic F-68 increases the post-thaw growth of cryopreserved plant cells. Cryobiology. 1996;33:508-14.

Birchenough et al., Topical poloxamer-188 improves blood flow following thermal injury in rat mesenteric microvasculature. Ann Plast Surg. May 2008;60(5):584-8.

Borgens et al., Subcutaneous tri-block copolymer produces recovery from spinal cord injury. J Neurosci Res. Apr. 1, 2004;76(1):141-54.

Boschert et al., Analysis of lipocyte viability after liposuction. Plast Reconstr Surg. Feb. 2002;109(2):761-5.

Bustamante et al., Alpha-lipoic acid in liver metabolism and disease. Free Radic Biol Med. Apr. 1998;24(6):1023-39.

Cho et al., Alpha-lipoic acid decreases thiol reactivity of the insulin receptor and protein tyrosine phosphatase 1B in 3T3-L1 adipocytes. Biochem Pharmacol. Sep. 1, 2003;66(5):849-58.

Diesel et al., Alpha-lipoic acid as a directly binding activator of the insulin receptor: protection from hepatocyte apoptosis. Biochemistry. Feb. 27, 2007;46(8):2146-55. Epub Feb 3, 2007.

Duenschede et al., Protective effects of ischemic preconditioning and application of lipoic acid prior to 90 min of hepatic ischemia in a rat model. World J Gastroenterol. Jul. 21, 2007;13(27):3692-8.

Dulundu et al., Alpha-lipoic acid protects against hepatic ischemia-reperfusion injury in rats. Pharmacology. 2007;79(3):163-70. Epub Jan. 24, 2007.

Eto et al., Characterization of structure and cellular components of aspirated and excised adipose tissue. Plast Reconstr Surg. Oct. 2009;124(4):1087-97.

Ferguson et al., The viability of autologous fat grafts harvested with the LipiVage system: a comparative study. Ann Plast Surg. May 2008;60(5):594-7.

Giugliano et al., Liposuction and lipoinjection treatment for congenital and acquired lipodystrophies in children. Plast Reconstr Surg. Jul. 2009;124(1):134-43.

Gonzalez et al., An alternative method for harvest and processing fat grafts: an in vitro study of cell viability and survival. Plast Reconstr Surg. Jul. 2007;120(1):285-94.

González Hernández et al., Serum-free culturing of mammalian cells—adaptation to and cryopreservation in fully defined media. ALTEX. 2007;24(2):110-6.

Greene et al., alpha-Lipoic acid prevents the development of glucose-induced insulin resistance in 3T3-L1 adipocytes and accelerates the decline in immunoreactive insulin during cell incubation. Metabolism. Sep. 2001;50(9):1063-9.

Greenebaum et al., Poloxamer 188 prevents acute necrosis of adult skeletal muscle cells following high-dose irradiation. Burns. Sep. 2004;30(6):539-47.

Gull et al., Viability of the human adenocarcinoma cell line Caco-2: Influence of cryoprotectant, freezing rate, and storage temperature. Sci Pharm. 2009;77:133-41.

Haramaki et al., Cytosolic and mitochondrial systems for NADH- and NADPH-dependent reduction of alpha-lipoic acid. Free Radic Biol Med. 1997;22(3):535-42.

Hyakusoku et al., Complications after autologous fat injection to the breast. Plast Reconstr Surg. Jan. 2009;123(1):360-70.

Kaufman et al., Autologous fat transfer national consensus survey: trends in techniques for harvest, preparation, and application, and perception of short- and long-term results. Plast Reconstr Surg. Jan. 2007;119(1):323-31.

Khattak et al., Pluronic F127 as a cell encapsulation material: utilization of membrane-stabilizing agents. Tissue Eng. May-Jun. 2005;11(5-6):974-83.

Kiemer et al., Inhibition of LPS-induced nitric oxide and TNF-alpha production by alpha lipoic acid in rat Kupffer cells and in RAW 264.7 murine macrophages. Immunol Cell Biol. Dec. 2002;80(6):550-7.

Kurita et al., Influences of centrifugation on cells and tissues in liposuction aspirates: optimized centrifugation for lipotransfer and cell isolation. Plast Reconstr Surg. Mar. 2008;121(3):1033-41.

Lam et al., Limitations, complications, and long-term sequelae of fat transfer. Facial Plast Surg Clin North Am. Nov. 2008;16(4):391-9.

Lee et al., A novel approach to adipocyte analysis. Plast Reconstr Surg. Feb. 2012;129(2):380-7.

Liu et al., Neuroprotective Effect of lipoic acid in Cerebral Ischemia-reperfusion Injury of Rats. Chin J Vet Sci. Jul. 2004;24(4):388-90. Chinese.

Lowe et al., Beneficial effects of Pluronic F-68 and artificial oxygen carriers on the post-thaw recovery of cryopreserved plant cells. Artif Cells Blood Substit Immobil Biotechnol. Jul. 2001;29(4):297-316.

Medina et al., A high-throughput model for fat graft assessment. Lasers Surg Med. Dec. 2009;41(10):738-44.

Medina et al., Polymer therapy: a novel treatment to improve fat graft viability. Plast Reconstr Surg. Jun. 2011;127(6):2270-82.

Merchant et al, Poloxamer 188 enhances functional recovery of lethally heat-shocked fibroblasts. J Surg Res. Feb. 1, 1998;74(2):131-40.

Moini et al., R-alpha-lipoic acid action on cell redox status, the insulin receptor, and glucose uptake in 3T3-L1 adipocytes. Arch Biochem Biophys. Jan. 15, 2002;397(2):384-91.

Monteiro et al., Adipocyte size and liability to cell death. Obes Surg. Jun. 2006;16(6):804-6.

Müller et al., Alpha-lipoic acid preconditioning reduces ischemia-reperfusion injury of the rat liver via the PI3-kinase/Akt pathway. Am J Physiol Gastrointest Liver Physiol. Oct. 2003;285(4):G769-78. Epub Jun. 19, 2003.

Nguyen et al., Enhanced Fat Protection and Survival in Fat Transplantation via Treatment with Poloxamer 188. IFATS08 Symposium 6. France. Oct. 2008. Journal of Surgical Research. Feb. 2, 2009; 151(2); 210-11. Abstract 87.

Nishimura et al., Microvascular angiogenesis and apoptosis in the survival of free fat grafts. Laryngoscope. Aug. 2000;110(8):1333-8.

Ogawa et al., The effect of hydrostatic pressure on three-dimensional chondroinduction of human adipose-derived stem cells. Tissue Eng Part A. Oct. 2009;15(10):2937-45.

Packer, alpha-Lipoic acid: a metabolic antioxidant which regulates NF-kappa B signal transduction and protects against oxidative injury. Drug Metab Rev. May 1998;30(2):245-75.

Palmer et al., Surfactant administration reduces testicular ischemia-reperfusion injury. J Urol. Jun. 1998;159(6):2136-9.

Pearson, Human genetics: One gene, twenty years. Nature. Jul. 2009;460:164-9.

Pessler et al., Oxidative stress impairs nuclear proteins binding to the insulin responsive element in the GLUT4 promoter. Diabetologia. Dec. 2001;44(12):2156-64.

Potier et al., Prolonged hypoxia concomitant with serum deprivation induces massive human mesenchymal stem cell death. Tissue Eng. Jun. 2007;13(6):1325-31.

Pu et al., Autologous fat grafts harvested and refined by the Coleman technique: a comparative study. Plast Reconstr Surg. Sep. 2008;122(3):932-7.

Pu et al., The viability of fatty tissues within adipose aspirates after conventional liposuction: a comprehensive study. Ann Plast Surg. Mar. 2005;54(3):288-92; discussion 292.

Ramon et al., Enhancing the take of injected adipose tissue by a simple method for concentrating fat cells. Plast Reconstr Surg. Jan. 2005;115(1):197-201.

Rohrich et al., In search of improved fat transfer viability: a quantitative analysis of the role of centrifugation and harvest site. Plast Reconstr Surg. Jan. 2004;113(1):391-5.

Roy et al., Antioxidant regulation of phorbol ester-induced adhesion of human Jurkat T-cells to endothelial cells. Free Radic Biol Med. Jul. 15, 1998;25(2):229-41.

Roy et al., Redox regulation of cell functions by alpha-lipoate: biochemical and molecular aspects. Biofactors. 1998;7(3):263-7.

Rudich et al., Lipoic acid protects against oxidative stress induced impairment in insulin stimulation of protein kinase B and glucose transport in 3T3-L1 adipocytes. Diabetologia. Aug. 1999;42(8):949-57.

Schmolka, A review of block polymer surfactants. J Am Oil Chem Soc. 1977;54(3):110-6.

Shen et al., R-alpha-lipoic acid and acetyl-L-carnitine complementarily promote mitochondrial biogenesis in murine 3T3-L1 adipocytes. Diabetologia. Jan. 2008;51(1):165-74. Epub Nov. 17, 2007.

Suga et al., Numerical measurement of viable and nonviable adipocytes and other cellular components in aspirated fat tissue. Plast Reconstr Surg. Jul. 2008;122(1):103-14.

Thanik et al., A murine model for studying diffusely injected human fat. Plast Reconstr Surg. Jul. 2009;124(1):74-81.

Tharmalingam et al., Pluronic enhances the robustness and reduces the cell attachment of mammalian cells. Mol Biotechnol. Jun. 2008;39(2):167-77.

Wlotzka et al., In vivo properties of an anti-GnRH Spiegelmer: an example of an oligonucleotide-based therapeutic substance class. Proc Natl Acad Sci U S A. Jun. 25, 2002;99(13):8898-902. Epub Jun. 17, 2002.

Wu et al., Effects of poloxamer 188 on phospholipid monolayer morphology: an atomic force microscopy study. Langmuir. Feb. 17, 2009;25(4):2133-9.

Yamaguchi et al., Revascularization determines volume retention and gene expression by fat grafts in mice. Exp Biol Med (Maywood). Nov. 2005;230(10):742-8.

Yasuda et al., Dystrophic heart failure blocked by membrane sealant poloxamer. Nature. Aug. 18, 2005;436(7053):1025-9. Epub Jul. 17, 2005.

Yi et al., Enhancement of viability of fat grafts in nude mice by endothelial progenitor cells. Dermatol Surg. Dec. 2006;32(12):1437-43.

Zhu et al., Hypoxia and serum deprivation-induced apoptosis in mesenchymal stem cells. Stem Cells. Feb. 2006;24(2):416-25. Epub Oct. 27, 2005.

Zhu et al., Supplementation of fat grafts with adipose-derived regenerative cells improves long-term graft retention. Ann Plast Surg. Feb. 2010;64(2):222-8.

* cited by examiner

POE
(HYDROPHILIC)

POE UNIT    POP UNIT    POE UNIT
(HYDROPHILIC) (HYDROPHOBIC) (HYDROPHILIC)

POLYOXYETHYLENE—POLYOXYPROPYLENE—POLYOXYETHYLENE

METHOD OF PREVENTING FAT GRAFT RESORPTION BY ADMINISTERING FAT-DERIVED CELLS AND POLOXAMER P 188

RELATED APPLICATIONS

The present application claims priority under 35 U.S.C. §119(e) to U.S. provisional patent application, U.S. Ser. No. 61/107,023, filed Oct. 21, 2008, which is incorporated herein by reference.

BACKGROUND OF THE INVENTION

Soft tissue injuries and malformations secondary to trauma, congenital defects, infections, and oncologic resections are a source of significant morbidity in patients. At present autologous free flap reconstruction or local advancement flaps are the workhorses of reconstructive modalities for significant soft tissue and bony defects. While pedicled flaps and free flap reconstructions offer powerful tools for reconstruction, they are not without potentially serious side effects and donor site morbidity.

Autologous fat transplantation has been used in soft tissue reconstruction but is unpredictable. The advantage of using lipo-aspirated fat is two-fold: 1) minimal donor site morbidity providing a safe and readily accessible source for autologous cells, and 2) these procedures can be performed relatively easily without the concern for ischemic complications and early graft failures associated with vascularized free flaps. However, to date free fat grafts have been plagued with unpredictable high levels of reabsorption and resultant irregularities. Free fat graft failures and volume reduction appear to be related to mechanical stresses resulting in membrane damage from harvesting, early ischemic changes, and nutrient deprivation and insufficient vascular supply to the graft. These stressors lead to apoptosis and cell death. Subsequent, graft reabsorption results from removal of dead cellular debris following revascularization. This leads to inconsistent and undesirable results for soft tissue restoration. Since fat transplantation was first described by Neuber in 1893, little has been achieved to improve the results of free fat grafts. Thus far, efforts to attentuate the initial ischemic insult cells until sufficient vascularity can be established have been met with modest results. Thus, improving the vascular supply of the fat transplant alone may not be sufficient to greatly improve the results of fat transplantation. Preventing damage to cells during the procurement, handling, and/or transplantation of the fat graft is also important.

There remains a need for more successful transplantation of adipose tissue or cells derived from adipose tissue (e.g., adipocytes, stem cells) in cosmetic and reconstructive surgery. The ability to transfer a large volume of autologous adipose tissue for soft tissue reconstruction would provide a novel reconstructive option for potentially millions of patients, without the associated donor site morbidities. Additionally, it would provide a powerful tool for patients who have poor donor site options, and patients with the inability to tolerate the extended operating times required in flap reconstructions.

SUMMARY OF THE INVENTION

The present invention stems from the need for predictable, successful transplantation of adipose tissue and adipocytes. The invention at least partly stems from the discovery that damaged cells in fat grafts become apoptotic and eventually are resorbed by the recipient's body. Preventing damage to the cells of such grafts, in particular the cell membranes, allows for more successful and predictable fat transplantation. In order to prevent damage to cells of the graft, in the present invention the cell membrane is protected from damage during procurement of the graft, handling of the graft (e.g., washing, storage), and/or finally the transplantation procedure. Various membrane stabilization agents have been studied to identify agents that decrease cell death in fat grafts over time. Triblock copolymers with a hydrophobic portion flanked by two hydrophlic portions (e.g., Poloxamer P188, shown in FIG. 1) have been found to stabilize cell membranes and decrease cell death in fat grafts over time. Such polymers mixed with adipose tissue or adipocytes to be transplanted lead to predictable and permanent fat transplantation. Other polymers, such as diblock copolymers, tetrablock copolymers, and polyethylene glycols, were tested and found to not protect cells from damage or to lyse the cells. Therefore, the present invention provides compositions, methods, and kits for using triblock copolymers, particularly P188, in fat transplantation for soft tissue reconstruction or augmentation.

Cell membranes include phospholipids that have hydrophobic and hydrophilic domains. These phospholipids form a continuous lipid bilayer that surrounds the cell. The integrity of this bilayer is important in preventing damage to the cell. The present invention provides compositions of triblock copolymers that seal and/or stabilize the cell membrane and prevent the cells from being damaged. Typically such polymers interact with the phospholipid bilayer of a cell and plug holes in the traumatized cell membrane. Additionally, such polymers have been shown to decrease the membrane viscosity. Decreased cellular viscosity allows the traumatized cells to become more soluble, which reduces the tension on the injured membranes. The invention also provides methods of using such compositions in the transplantation of adipose tissue and adipocytes, or other tissues and cells (e.g., stem cells).

In one aspect, the invention provides triblock copolymers that aid in sealing and/or stabilizing the membranes of cells. Preferably, the polymer utilized in the present invention is biocompatible and/or biodegradable. The polymer should not result in the lysis of cells. In certain embodiments, the polymer is a non-ionic polymer. In certain embodiments, the polymer is a polyether. In certain embodiments, the polymer is a polyalkylether. In certain embodiments, the polymer is a co-polymer of a polyalkylether and another polymer (e.g., a polyalkylether). In particular, poloxymers (also known as poloxamers) have been found useful in sealing and stabilizing cell membranes. As shown in the chemical structure below, poloxymers are non-ionic triblock copolymers composed of a central hydrophobic chain of polyoxypropylene (POP) (also known as polypropylene glycol) flanked by two hydrophilic chains of polyoxyethylene (POE) (also known as polyethylene glycol (PEG)). In certain embodiments, triblock copolymers with a hydrophobic core flanked by two hydrophilic tails are preferred in fat transplantation.

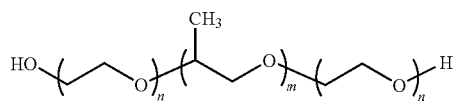

In certain embodiments, poloxymer P188 is used to seal and/or stabilize the membranes of cells of a fat graft. Poloxymer P188 has been found to be particularly effective in repairing damaged membranes of adipocytes and improving the viability and likelihood of survival of damaged adipocytes. Without wishing to be bound by a particular theory, a proposed mechanism for repair of cell membranes with P188 is illustrated in FIG. 2. A damaged cell membrane has exposed to its surroundings a portion of the central lipid layer (i.e., the hydrophobic portion of the membrane). The central hydrophobic portion of P188 interacts with this hydrophobic layer of the membrane, and the flanking hydrophilic ends of P188 locate themselves along the outer hydrophilic surface of the cell membrane. This sealing/repair process is analogous to a conventional automotive tire plug repair, in which the center of a flexible rubber plug is pushed into a small hole in a tire to seal it with the end of the plug being located along the outer tread. More than one P188 molecule may be needed to seal a hole in a damaged membrane. In certain embodiments, poloxymer P188 prevents damage to cells of a fat graft. Poloxamers are sold by BASF under the trade name PLURONIC®. In particular, poloxamer 188 (P188) is PLURONIC® F68. Since the lengths of the blocks making up the polymer can be customized, many different poloxamers with different properties exist. These copolymers are commonly named with a letter for the poloxamer's state at room temperature ("P" for powder, "L" for liquid, "F" for flake) followed by three digits. The first two digits x100 give the approximate molecular weight of the hydrophobic polyoxypropylene core, and the last digit x10 gives the percentage of polyoxyethylene content. Poloxamer 188 is a poloxymer with a polyoxypropylene molecular mass of 1800 g/mol and an 80% polyoxyethylene content, and poloxamer 188 has an average molecular weight of 7680-9510 g/mol. To convert the "Pxxy" name to the tradename "Fzz", the xx of "Pxxy" is multiplied by approximately 3, that is, P188 is F68. Other poloxymers that may be useful in the present invention include poloxamers P108 (PLURONIC® F38), P184 (PLURONIC® L64), P401, P402, P407 (PLURONIC® F127), and P408 (PLURONIC® F108). Other poloxamers with a lower molecular weight and approximately equal or lower PEG content may be useful in the present invention. The polymer is typically added to the cells as soon as the cells are removed from the donor to prevent and/or repair membrane damage as soon as possible. The polymer is added to the cells of the transplant graft at a concentration ranging from approximately 1 mg to approximately 20 mg of polymer per ml of cells. In certain embodiments, a millimolar concentration of the polymer is used in the polymer/cell composition for transplantation. Typically the lowest concentration of polymer that yields the desired membrane stabilization is used. As would be appreciated by one of skill in the art, the concentration of polymer in the composition will depend on the polymer being used to stabilize the cells being transplanted.

The cells or tissue to be transplanted are mixed with the polymer at the appropriate concentration and are then transplanted into the recipient (e.g., a human) at the desired transplant site (e.g., face, lips, breast). Any cells or tissue may be transplanted using the inventive technology. In certain embodiments, the tissue is adipose tissue. In certain embodiments, the cells are derived from fat tissue. In certain embodiments, the cells are part of a fat graft (i.e., adipose tissue) that contains different types of cells including, but not limited to, adipocytes, stromal cells, epithelial cells, endothelial cells, fibroblasts, and blood cells. In certain embodiments, the cells are adipocytes. In certain embodiments, the cells are fibroblasts. In certain embodiments, the cells are stromal cells. In certain embodiments, the cells are endothelial cells. In certain embodiments, the cells are stem cells. In certain embodiments, the cells are stem cells derived from adipose tissue.

The cells may be mixed with the polymer at the time of harvesting. In certain embodiments, the site where the adipose tissue is to be removed is injected with a composition including the polymer before the tissue is removed from the donor. In other embodiments, polymer is added to the cells after they have been removed from the donor. Polymer may also be added to the cells at the time of processing or storage, or the cells may be mixed with polymer just prior to transplantation. The cells or tissue may be washed or otherwise processed with a composition that includes the polymer. In certain embodiments, the polymer is washed from the graft prior to implantation.

The cell/polymer composition may also include other agents. For example, the composition may include agents that further protect or stabilize the cells to be transplanted, or the agent may protect the polymer. In certain embodiments, the composition includes vitamins, minerals, antioxidants, osmotic protectants, viscosity enhancers, coenzymes, membrane stabilization agents, lipids, carbohydrates, hormones, growth factors, anti-inflammatory agents, polynucleotides, proteins, peptides, alcohols, organic acids, small organic molecules, etc. A particularly useful combination in fat transplantation is P188 and lipoic acid (shown below in its reduced and oxidized forms). In certain embodiments, the reduced form of lipoic acid is used. In other embodiments, the oxidized form of lipoic acid is used. In still other embodiments, a mixture of the two forms is used.

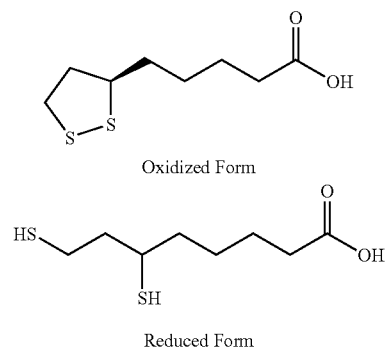

Oxidized Form

Reduced Form

The present invention provides compositions of adipocytes and a polymer (e.g., P188) for use in fat transplantation. In certain embodiments, the present invention provides compositions of stem cells and a polymer (e.g., P188). The stem cells may be adult stem cells derived from fat tissue. Other cells derived from fat tissue (e.g., stem cells, fibroblasts, endothelial cells, stromal cells) may also be used in the invention. The inventive cell/polymer compositions may include other agents that minimize membrane disruption and/or free radical formation (e.g., antioxidants, vitamins, lipids, proteins, peptides, hormones, growth factors, carbohydrates, pharmaceutical agents) as discussed herein.

In another aspect, the invention provides kits useful in transplanting fat using the inventive compositions and methods. The kit may include all or a subset of all the components necessary for transplanting fat or fat-derived cells into a subject. The kits may include, for example, polymer (e.g., P188), buffered solution(s) for washing cells, device for washing cells, cells, syringe, needle, cups, containers, alcohol swabs, anesthetics, antibiotics, antioxidants, vitamins, lipids, carbohydrates, hormones, growth factors, etc. In certain embodiments, a container or syringe used in harvesting the cells may have in it the polymer (e.g., P188) so that the harvested cells are immediately contacted with the membrane stabilization agent. In certain embodiments, the cells are acquired from the patient to receive the cells (i.e., an autologous graft). In certain embodiments, the components of the kit are sterilely packaged for convenient use by the surgeon or other health care professional. The kit may also include instructions for using the polymer (e.g., P188) and other agents in the harvesting/transplantation procedure. The kit may provide the necessary components for a single use. The kit may also include packaging and information as required by a governmental regulatory agency that regulates pharmaceuticals and/or medical devices.

DEFINITIONS

Figure 1A:
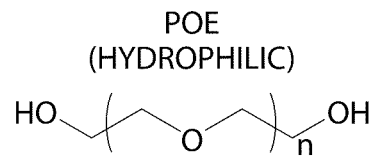
FIG. 1. A. Polyoxyethylene (POE) hydrophilic subunit of polymer P188. B. Triblock P188 structure with hydrophobic polyoxypropylene (POP) subunit spanning two POE hydrophilic tails.

"Adipose tissue," as used herein, refers to tissue that is composed of adipocytes. Adipose tissue is typically loose connective tissue composed of adipocytes. The main role in the body is to store energy in the form of fat; however, adipose tissue also insulates and protects the body as well as acting as an endocrine organ. Adipose tissue can be white adipose tissue or brown adipose tissue. The term "adipose tissue" is used interchangeably with "fat tissue."

"Anti-inflammatory agent," as used herein, refers to any substance that inhibits one or more signs or symptoms of inflammation.

The term "approximately" in reference to a number generally includes numbers that fall within a range of 5% in either direction of the number (greater than or less than the number) unless otherwise stated or otherwise evident from the context (except where such number would exceed 100% of a possible value).

"Biocompatible" refers to a material that is substantially nontoxic to a recipient's cells in the quantities and at the location used, and also does not elicit or cause a significant deleterious or untoward effect on the recipient's body at the location used, e.g., an unacceptable immunological or inflammatory reaction, unacceptable scar tissue formation, etc.

"Biodegradable" means that a material is capable of being broken down physically and/or chemically within cells or within the body of a subject, e.g., by hydrolysis under physiological conditions and/or by natural biological processes such as the action of enzymes present within cells or within the body, and/or by processes such as dissolution, dispersion, etc., to form smaller chemical species which can typically be metabolized and, optionally, used by the body, and/or excreted or otherwise disposed of. For purposes of the present invention, a polymer or hydrogel whose molecular weight decreases over time in vivo due to a reduction in the number of monomers is considered biodegradable.

The terms "polynucleotide", "nucleic acid", or "oligonucleotide" refer to a polymer of nucleotides. The terms "polynucleotide", "nucleic acid", and "oligonucleotide", may be used interchangeably. Typically, a polynucleotide comprises at least two nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, 2'-methoxyribose, 2'-aminoribose, ribose, 2'-deoxyribose, arabinose, and hexose), or modified phosphate groups (e.g., phosphorothioates and 5'-N phosphoramidite linkages). Enantiomers of natural or modified nucleosides may also be used. Nucleic acids also include nucleic acid-based therapeutic agents, for example, nucleic acid ligands, siRNA, short hairpin RNA, antisense oligonucleotides, ribozymes, aptamers, and SPIEGELMERS™, oligonucleotide ligands described in Wlotzka et al., *Proc. Natl. Acad. Sci. USA*, 2002, 99(13):8898, the entire contents of which are incorporated herein by reference.

A "polypeptide", "peptide", or "protein" comprises a string of at least three amino acids linked together by peptide bonds. The terms "polypeptide", "peptide", and "protein", may be used interchangeably. Peptide may refer to an individual peptide or a collection of peptides. Inventive peptides preferably contain only natural amino acids, although non natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, or other modifications. None of the modifications should substantially interfere with the desired biological activity of the peptide.

The terms "polysaccharide" and "carbohydrate" may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose. (e.g., 2'-fluororibose, deoxyribose, and hexose). Carbohydrates may exist in many different forms, for example, conformers, cyclic forms, acyclic forms, stereoisomers, tautomers, anomers, and isomers.

"Small molecule" refers to organic compounds, whether naturally occurring or artificially created (e.g., via chemical synthesis) that have relatively low molecular weight and that are not proteins, polypeptides, or nucleic acids. Small molecules are typically not polymers with repeating units. In certain embodiments, a small molecule has a molecular weight of less than about 1500 g/mol. In certain embodiments, the molecular weight of the polymer is less than about 1000 g/mol. Also, small molecules typically have multiple carbon-carbon bonds and may have multiple stereocenters and functional groups.

"Subject," as used herein, refers to an individual to whom an agent is to be delivered, e.g., for experimental, diagnostic, and/or therapeutic purposes. Preferred subjects are mammals, particularly domesticated mammals (e.g., dogs, cats, etc.), primates, or humans. In certain embodiments, the subject is a human. In certain embodiments, the subject is an experimental animal such as a mouse or rat. A subject under the care of a physician or other health care provider may be referred to as a "patient."

"Pharmaceutical agent," also referred to as a "drug," is used herein to refer to an agent that is administered to a subject to treat a disease, disorder, or other clinically recognized condition that is harmful to the subject, or for prophylactic purposes, and has a clinically significant effect on the body to treat or prevent the disease, disorder, or condition. Therapeutic agents include, without limitation, agents listed in the United States Pharmacopeia (USP), *Goodman and Gilman's The Pharmacological Basis of Therapeutics,* 10th Ed., McGraw Hill, 2001; Katzung, B. (ed.) *Basic and Clinical Pharmacology,* McGraw-Hill/Appleton & Lange; 8th edition (Sep. 21, 2000); *Physician's Desk Reference* (Thomson Publishing), and/or *The Merck Manual of Diagnosis and Therapy,* 17th ed. (1999), or the 18th ed (2006) following its publication, Mark H. Beers and Robert Berkow (eds.), Merck Publishing Group, or, in the case of animals, *The Merck Veterinary Manual,* 9th ed., Kahn, C. A. (ed.), Merck Publishing Group, 2005.

DETAILED DESCRIPTION OF CERTAIN EMBODIMENTS OF THE INVENTION

The present invention stems from the recognition that the transplantation of adipose tissue or adipocytes in cosmetic and reconstructive surgery may be improved by the addition of a polymer that stabilizes the membranes of the cells in the graft. Without wishing to be bound by a particular theory, the polymer is thought to interact with the cell membranes and seal or prevent defects in the membrane, thereby preventing or minimizing injury to the cell (e.g., ion leakage). Preventing injury to the cells reduces the extent of apoptosis and cell death in the graft and aids in improving the success and consistency of fat transplants in soft tissue restoration, reconstruction, or augmentation. The present invention provides polymers, compositions, methods, and kits for improving fat transplantation in a subject (e.g., human).

Polymers

The present invention is based on the discovery of certain polymers that stabilize the cell membranes of cells in fat transplants or cells derived from adipose tissue (e.g., stem cells, stromal cells, fibroblasts, endothelial cells, epithelial cells). The polymer is mixed with the cells at a sufficient concentration to stabilize and protect the membranes of the cells from damage and/or to seal already damaged membranes. Such polymers may be used in conjunction with other methods of improving the success of fat transplantation including, for example, improving the vascular supply of the graft or adding other agents that help to prevent injury to the cells to be transplanted (e.g., lipoic acid).

Any polymer that interacts with and stabilizes cell membranes may be added to cells used in a fat transplant; however, triblock copolymers with a hydrophobic central portion flanked by two hydrophilic tails have been found to be particularly useful in improving fat grafts. In certain embodiments, the polymer is a synthetic polymer (i.e., a polymer not produced in nature). In other embodiments, the polymer is a natural polymer (e.g., a protein, polysaccharide, rubber).

In certain embodiments, the polymer is a surface active polymer. In certain embodiments, the polymer is a non-ionic polymer. In certain embodiments, the polymer is a non-ionic block copolymer.

In certain embodiments, the polymer includes a polyether portion. In certain embodiments, the polymer includes a polyalkylether portion. In certain embodiments, the polymer includes polyethylene glycol tails. In certain embodiments, the polymer includes a polypropylene glycol central portion. In certain embodiments, the polymer includes polybutylene glycol as the central portion. In certain embodiments, the polymer includes polypentylene glycol as the central portion. In certain embodiments, the polymer includes polyhexylene glycol as the central portion. In certain embodiments, the polymer is a triblock copolymer of one of the polymers described herein.

In certain embodiments, the polymer is a triblock copolymer of a polyalkyl ether (e.g., polyethylene glycol, polypropylene glycol) and another polymer. In certain embodiments, the polymer is a triblock copolymer of a polyalkyl ether and another polyalkyl ether. In certain embodiments, the polymer is a triblock copolymer of polyethylene glycol and another polyalkyl ether. In certain embodiments, the polymer is a triblock copolymer of polypropylene glycol and another polyalkyl ether. In certain embodiments, the polymer is a triblock copolymer with at least one unit of polyalkyl ether. In certain embodiments, the polymer is a triblock copolymer of two different polyalkyl ether. In certain embodiments, the polymer is a triblock copolymer including a polyethylene glycol unit. In certain embodiments, the polymer is a triblock copolymer including a polypropylene glycol unit. In certain embodiments, the polymer is a triblock copolymer of a more hydrophobic unit flanked by two more hydrophilic units. In certain embodiments, the hydrophilic units are the same type of polymer. In certain embodiments, the polymer includes a polypropylene glycol unit flanked by two more hydrophilic units. In certain embodiments, the polymer includes two polyethylene glycol units flanking a more hydrophobic unit. In certain embodiments, the polymer is a triblock copolymer with a polypropylene glycol unit flanked by two polyethylene glycol units. In certain embodiments, the polymer is of the formula:

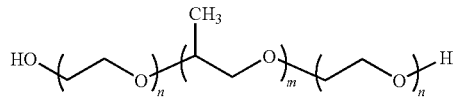

wherein n is an integer between 2 and 200, inclusive; and m is an integer between 2 and 200, inclusive. In certain embodiments, n is an integer between 10 and 100, inclusive. In certain embodiments, m is an integer between 5 and 50 inclusive. In certain embodiments, n is approximately 2 times m. In certain embodiments, n is approximately 70, and m is approximately 35. In certain embodiments, n is approximately 50, and m is approximately 30. In certain embodiments, the polymer is poloxamer P188, which is marketed by BASF under the trade name PLURONIC® F68. Other PLURONIC® polymers that may be useful in the present invention include, but are not limited to, PLURONIC® F108, PLURONIC® F127, PLURONIC® F38, PLURONIC® F68, PLURONIC® F77, PLURONIC® F87, PLURONIC® F88, PLURONIC® F98, PLURONIC® L10, PLURONIC® L101, PLURONIC® L121, PLURONIC® L31, PLURONIC® L35, PLURONIC® L43, PLURONIC® L44, PLURONIC® L61, PLURONIC® L62, PLURONIC® L64, PLURONIC® L81, PLURONIC® L92, PLURONIC® N3, PLURONIC® P103, PLURONIC® P104, PLURONIC® P105, PLURONIC® P123, PLURONIC® P65, PLURONIC® P84, and PLURONIC® P85. Poloxamers are generally synthesized by the sequential addition of first propylene oxide and then ethylene oxide to propylene glycol.

Figure 2:
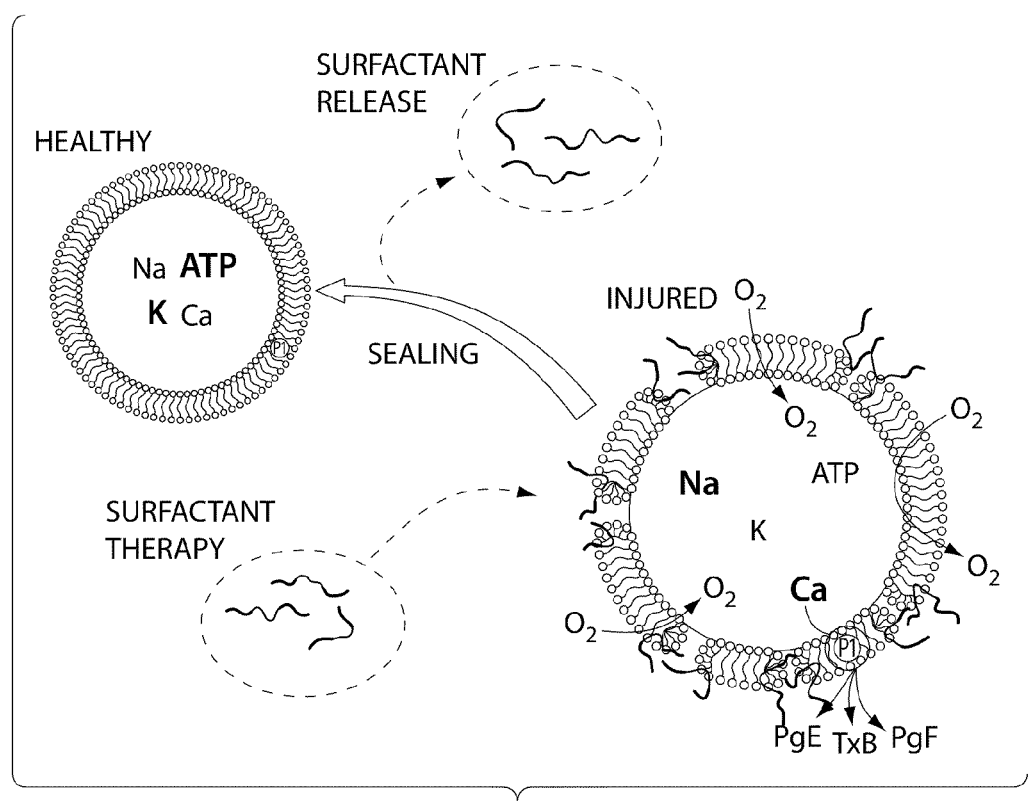
FIG. 2. Putative membrane insertion of P188. Hydrophobic regions of P188 are thought to insert into the pores of damaged membranes with the long, hydrated hydrophilic tails extending beyond the membrane decreasing cellular viscosity and stabilizing membrane ionic leakage.

As demonstrated in the Examples below, triblock copolymers have the ability to insert themselves into traumatized adipocyte membranes, allowing for stabilization of the membrane (see FIG. 2). Furthermore, such polymers are known to decrease the membrane viscosity with their highly hydrated polyethylene glycol tails. By decreasing cellular viscosity they allow the traumatized cells to become more soluble, thus decreasing the tension on the injure membrane. In particular, P188, a commercially available triblock copolymer, has been shown to be particularly effective for repairing damaged membranes and improving the viability and likelihood of survival of damaged adipocytes. The effectiveness of P188 in the rescue of injured adipocytes in the peritransplant period (the time from harvesting to stable engraftment) is demonstrated in the Examples below which look at the histology, weight of the fat graft over time, apoptosis events, cell viability, and raw DNA content. P188 is shown to be more effective than any of the other polymers tested even smaller and larger triblock copolymers with the same order of blocks do not perform as well. Diblock and tetrablock copolymers even appear to be toxic to grafts.

P188 has been shown to be poorly soluble in adipose tissue, and it is not absorbed well onto intact, uninjured membranes. P188 allows adipocytes that have suffered mechanical sheer injury from the harvesting process to maintain their normal membrane mechanics. Once these cells are able to repair their membranes by increasing the amount of phospholipids in the bilayer, P188 is mechanically extruded [Agarwal, J., A. Walsh, and R. C. Lee, *Multimodal strategies for resuscitating injured cells. Ann N Y Acad Sci,* 2005. 1066:295-309; incorporated herein by reference]. The extrusion of P188 is caused by the increase in transmembrane surface pressure. Once extruded from the transplanted cells, P188 is excreted essentially unchanged by the kidneys, with a small amount excreted through the biliary enteric system [Singh-Joy, S. D. and V. C. McLain, *Safety assessment of poloxamers* 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and 407, poloxamer 105 benzoate, and poloxamer 182 dibenzoate as used in cosmetics. *Int J Toxicol,* 2008. 27 Suppl 2:93-128; incorporated herein by reference]. There is no evidence of adverse effects or safety concerns with P188 at the concentrations useful in fat transplantation.

The molecular weight of the polymer utilized in the present invention may range from approximately 500 g/mol up to approximately 50,000 g/mol. In certain embodiments, the molecular weight of the polymer ranges from approximately 1,000 g/mol to approximately 30,000 g/mol. In certain embodiments, the molecular weight of the polymer ranges from approximately 2,000 g/mol to approximately 15,000 g/mol. In certain embodiments, the molecular weight of the polymer ranges from approximately 2,000 g/mol to approximately 12,000 g/mol. In certain embodiments, the molecular weight of the polymer ranges from approximately 1,000 g/mol to approximately 5,000 g/mol. In certain embodiments, the molecular weight of the polymer ranges from approximately 5,000 g/mol to approximately 10,000 g/mol. In certain embodiments, the molecular weight of the polymer ranges from approximately 7,500 g/mol to approximately 10,000 g/mol. In certain embodiments, the molecular weight of the polymer ranges from approximately 10,000 g/mol to approximately 15,000 g/mol. In certain embodiments, the molecular weight of the polymer ranges from approximately 15,000 g/mol to approximately 20,000 g/mol. In certain embodiments, the molecular weight of the polymer ranges from approximately 1,000 g/mol to approximately 10,000 g/mol. In certain embodiments, the molecular weight of the polymer ranges from approximately 2,000 g/mol to approximately 10,000 g/mol. In certain embodiments, the molecular weight of the polymer ranges from approximately 3,000 g/mol to approximately 10,000 g/mol. In certain embodiments, the molecular weight of the polymer is approximately 20,000 g/mol to approximately 25,000 g/mol. In certain embodiments, the average molecular weight of the polymer is approximately 5,000 g/mol, approximately 5,500 g/mol, approximately 6,000 g/mol, 6,500 g/mol, 7,000 g/mol, approximately 7,500 g/mol, approximately 8,000 g/mol, approximately 8,500 g/mol, approximately 9,000 g/mol, approximately 9,500 g/mol, or approximately 10,000 g/mol. In certain embodiments, the average molecular weight of P188 is approximately 8,400 g/mol. The average molecular weight of other commercially available poloxamers are known in the art.

The composition of polymer used in the present invention is typically pharmaceutical grade material for use in humans and/or other animals. In certain embodiments, the polymer is approved for use in humans and for veterinary use. In some embodiments, the polymer is approved by United States Food and Drug Administration. In some embodiments, the polymer is pharmaceutical grade material. In some embodiments, the polymer meets the standards of the United States Pharmacopoeia (USP), the European Pharmacopoeia (EP), the British Pharmacopoeia, and/or the International Pharmacopoeia. In certain embodiments, the polymer is at least 90% pure. In certain embodiments, the polymer is at least 95% pure. In certain embodiments, the polymer is at least 98% pure. In certain embodiments, the polymer is at least 99% pure. In certain embodiments, the polymer is at least 99.5% pure. In certain embodiments, the polymer is at least 99.9% pure. In certain embodiments, the polymer is at least 99.99% pure. In certain embodiments, the polymer is free of toxic or non-biocompatible materials.

The polymer useful in the present invention typically degrades in vivo into non-toxic degradation products or is safely excreted by the body. The polymer is preferably biocompatible and does not result in any substantial unwanted side effects. The polymer's half-life in vivo can range from approximately 1 day to approximately 1 month. In certain embodiments, the half-life of the polymer in vivo ranges from approximately 1 day to approximately 1 week. In certain embodiments, the half-life of the polymer in vivo ranges from approximately 1 week to approximately 2 weeks. In certain embodiments, the half-life of the polymer in vivo ranges from approximately 3 weeks to approximately 4 weeks.

Polymers may be tested for use in fat transplantation by mixing a test polymer with fat cells to be transplanted and transplanting the resulting composition in a mouse or other rodent to determine over time the success of the fat implant (as described in the Examples below). Fat implants may be evaluated by various biochemical and pathological measurements, for example, weight of the implant, volume of the implant, histology, assessing markers of apoptosis and/or cell death, measuring number of live cells, assessing mitochondrial ATP levels, assessing DNA levels, or real-time PCR to determine levels of leptin, PPARγ2, or other markers. In certain embodiments, the testing is performed in nude mice. Polymers may also be screened in vitro by mixing cells with a test polymer and assaying the cells for markers of apoptosis or cell death, assaying the cells for toxicity, etc. In certain embodiments, the results using a test polymer are compared to the results from a control. In certain embodiments, the control polymer is P188. In certain embodiments, the control polymer is dextran. In certain embodiments, the control fat transplant is treated with normal saline.

The polymer may be combined with other biologically active agents and/or pharmaceutically acceptable excipients to form a composition useful for adding to cells to be transplanted. Such biologically active agents may also work to prevent cell death in a fat graft. Excipients may be used to aid in mixing the polymer with the cells to be transplanted or handling and storage of the resulting polymer/cell composition.

Biologically active agents that may be added along with a polymer to the cells to be transplanted include, but are not limited to, antioxidants, vitamins, membrane stabilizers, minerals, osmotic protectants, coenzymes, viscosity enhancers, hormones, and growth factors. Numerous mechanisms have been implicated in the cause of cell death in transplanted cells, for example, membrane disruption and free radical formation. Antioxidants may be used in fat transplantation to reduce free radical formation. Antioxidants scavenge free radicals and prevent damage caused by reactive oxygen species. In certain embodiments, a polymer/cell composition further comprises an antioxidant. The polymer and antioxidant are thought to improve protection of the cells and thereby improve fat grafting results. The antioxidants may be enzymatic or nonenzymatic antioxidants. Enzymatic antioxidants include, for example, superoxide dismutase, glutathione peroxidase, and catalase. Exemplary non-enzymatic antioxidants include alpha-tocopherol (vitamin E), vitamin A, glutathione, carotenoids (e.g., lycopene, lutein, polyphenols, β-carotene), flavonoids, flavones, flavonols, glutathione, N-acetyl cysteine, cysteine, lipoic acid, ubiquinal (coenzyme Q), ubiquinone (coenzyme Q10), melatonin, lycopene, butylated hydroxyanisole, butylated hydroxytoluene (BHT), benzoates, methyl paraben, propyl paraben, proanthocyanidins, mannitol, and ethylenediamine tetraacetic acid (EDTA). In certain embodiments, the antioxidant is a metallic antioxidant. In certain embodiments, the antioxidant is selenium. In certain embodiments, the antioxidant is zinc. In certain embodiments, the antioxidant is copper. In certain embodiments, the antioxidant is germanium.

In certain embodiments, a polymer/cell composition further comprises a vitamin. The vitamin may be an antioxidant. In certain embodiments, the vitamin is alpha-tocopherol (vitamin E). In certain embodiments, the vitamin is coenzyme Q10. In certain embodiments, the vitamin is beta-carotene. Other vitamins that may be added to the inventive polymer/cell composition include vitamin A, vitamin $B_1$ (thiamine), vitamin $B_2$ (riboflavin), vitamin $B_3$ (niacin), vitamin $B_4$ (adenine), vitamin $B_5$ (pantothenic acid), vitamin $B_6$ (pyridoxine), vitamin $B_7$ (biotin), vitamin $B_9$ (folic acid), vitamin $B_{12}$ (cyanocobalamin), vitamin D (ergocalciferol), and vitamin K.

In certain embodiments, a polymer/cell composition further comprises a hormone or growth factor. In certain embodiments, the hormone or growth factor is insulin, glitazones, cholesterol, VEGF, FGF, EGF, PDGF, etc. In certain embodiments, the polymer/cell composition further comprises an organic acid (e.g., lipoic acid). In certain embodiments, the polymer/cell composition further comprises a thiol-containing or disulfide-containing molecule (e.g., lipoic acid, glutathione). In certain embodiments, the polymer/cell composition further comprises a small organic molecule (e.g., anthocyanins, capsaicins).

In certain embodiments, fat cells are combined with P188 and glutathione for transplantation into a subject. In certain embodiments, fat cells are combined with P188 and lipoic acid for transplantation into a subject. In certain embodiments, fat cells are combined with P188 and vitamin E for transplantation into a subject.

The formulations of the polymers described herein may be prepared by any method known or hereafter developed in the art of pharmaceuticals. In general, such preparatory methods include the step of bringing the polymer into association with one or more excipients and/or one or more other biologically active agents. The relative amounts of the polymer, the pharmaceutically acceptable excipient(s), and/or any additional agents in a composition of the invention will vary, depending upon the identity of the polymer, size of the polymer, implantation site, and/or subject. By way of example, the composition to be mixed with cells to be transplanted may comprise between 1% and 99% (w/w) of the polymer.

Formulations of the polymer may comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular formulation desired. Remington's The Science and Practice of Pharmacy, 21$^{st}$ Edition, A. R. Gennaro, (Lippincott, Williams & Wilkins, Baltimore, Md., 2006; incorporated herein by reference) discloses various excipients used in formulating pharmaceutical compositions and known techniques for the preparation thereof. Except insofar as any conventional excipient is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of the polymer compositions include, but are not limited to, inert diluents, dispersing agents, surface active agents and/or emulsifiers, disintegrating agents, preservatives, buffering agents, lubricating agents, and/or oils. Such excipients may optionally be included in the inventive formulations. Excipients such as coloring agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus®, Phenonip®, methylparaben, Germall 115, Germaben II, Neolone™, Kathon™, and Euxyl®. In certain embodiments, the preservative is an antioxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

The inventive polymer besides being combined with the cells to be transplanted may be combined with one or more biologically active agents. In certain embodiments, the polymer is combined with an antioxidant. In certain embodiments, the polymer is combined with a vitamin. In certain embodiments, the polymer is combined with a lipid. In certain embodiments, the polymer is combined with a membrane stabilizer. In certain embodiments, the polymer is combined with a pharmaceutical agent. In certain embodiments, the polymer is combined with an anti-inflammatory agent. In certain embodiments, the polymer is combined with an antibiotic. In certain embodiments, the polymer is combined with a protein or peptide. In certain embodiments, the polymer is combined with a hormone. In certain embodiments, the polymer is combined with a growth factor. In certain embodiments, the polymer is combined with a carbohydrate. In certain embodiments, the polymer is combined with a liquid excipient for administering the polymer/cell composition. In certain embodiments, the excipient is an aqueous solution. In certain embodiments, the excipient is a buffered aqueous solution. In certain embodiments, the excipient is phosphate-buffered saline solution. In certain embodiments, the excipient is isotonic with extracellular fluid.

Uses

The invention provides methods of associating the polymer or polymer composition with cells to be transplanted before transplantation. The inventive system is particularly useful in improving the success of fat transplantation or improving the success of the transplantation of adipose tissue or cells derived from adipose tissue. Cells to be transplanted are mixed with a polymer at a sufficient concentration for the membranes of the cells to be stabilized and prevent damage of the cells during the transplantation. The polymer is thought to fix or prevent damage to the cell membranes by associating with the membrane. The cells or a composition of cells are mixed with the polymer or a composition comprising the polymer before transplantation into a subject. The polymer may be mixed with the cells at the time of procurement of the cells, during the storage or handling of the cells, or just prior to implantation of the cells into a subject.

The polymer may be mixed with the tissue or cells to be transplanted any time during the procurement, handling, processing, or implantation of the graft. In certain embodiments, the site where the cells or tissue are to be taken is injected with a composition of the polymer before the cells or tissue are harvested from the donor site. For example, the polymer may be include the tumescent injection solution (i.e., fluid that is injected into the donor site prior to liposuction) during the harvesting of the fat. In certain embodiments, the cells or tissue to be transplanted are contacted with the polymer as soon as they are harvested to protect them from damage. For example, after fat tissue is harvested from a donor (e.g., by liposuction or by a needle aspirate), it may be immediately contacted with the polymer. In certain embodiments, the polymer is included in the lipoaspirate collection container. In certain embodiments, the cells to be transplanted are harvested from the same person receiving them (i.e., an autologous donation). In certain embodiments, the cells are harvested from the stomach, thigh, or buttocks of the donor. In certain embodiments, the adipose tissue is harvested into a syringe or other container that already includes the polymer or a composition of the polymer. In other embodiments, the adipose tissue is harvested and immediately added to a composition of the polymer, or a composition of polymer is added to the fat tissue. The resulting polymer/cell composition may be further processed before implantation into a subject. For example, the cells may be washed, purified, extracted, or otherwise treated before implantation into a subject. In certain embodiments, the cells or tissue are kept in contact with an excess of the polymer throughout the processing of the cells for transplantation. In certain embodiments, excess polymer or polymer solution is removed from the tissue or cells to be transplanted, for example, by centrifugation. In certain embodiments, the polymer is washed from the graft prior to implantation.

In certain embodiments, the cells to be transplanted are contacted with the polymer immediately before transplantation. For example, the cells may be mixed with the polymer in the operating room or clinic just prior to implantation into a subject. The sterile polymer or composition thereof is mixed with the cells to be transplanted.

The cells are typically mixed with the polymer at a concentration ranging from approximately 1-20 mg of polymer per mL of cells. As would be appreciated by one of skill in the art, the concentration of polymer needed to sufficiently stabilize the membranes of the cells to be transplanted may vary depending on the polymer used, the subject, the site of implantation, etc. In certain embodiments, the concentration ranges from approximately 1-10 mg of polymer per mL of cells. In certain embodiments, the concentration ranges from approximately 1-5 mg of polymer per mL of cells. In certain embodiments, the concentration ranges from approximately 5-10 mg of polymer per mL of cells. In certain embodiments, the concentration ranges from approximately 10- 15 mg of polymer per mL of cells. In certain embodiments, the concentration ranges from approximately 15-20 mg of polymer per mL of cells. In certain embodiments, the concentration ranges from about 5 mg to about 15 mg of polymer per ml of cells. In certain embodiments, the concentration is approximately 5, 6, 7, 8, 9, 10, 11, 12, 13, 14, or 15 mg of polymer per mL of cells. In certain embodiments, when poloxymer P188 is used, the concentration is approximately 10 mg of polymer per mL of cells.

After the cells are contacted with the polymer, the cell/polymer composition is administered to or implanted into a subject. In certain embodiments, the cells are transplanted into the recipient within 0.5-6 hours of harvesting. In certain embodiments, the subject is a human. In certain embodiments, the subject is a mammal. In certain embodiments, the subject is a test animal such as a mouse, rat, rabbit, or dog. The cell/polymer composition is typically administered to a patient in need of a fat transplant. The subject may be undergoing reconstructive or cosmetic surgery. In certain embodiments, the fat transplantation is used in removing wrinkles. In certain embodiments, fat transplantation is used in soft tissue replacement or augmentation. In certain embodiments, fat transplantation is used in augmentation of the lips, cheeks, breasts, face, buttocks, calves, pectorals, and penis. Typically, autologous fat cells are transplanted back into the donor at a different site from which the cells were taken. The cells or tissue may be implanted or administered using any method or technique (e.g., injection, surgical implantation).

Besides adipocytes, fat tissue has been found to be a source of stem cells (Gimble et al., "Adipose-Derived Stem Cells for Regenerative Medicine" *Circulation Research* 100:1249-1260, 2007; incorporated herein by reference). Therefore, the inventive system may be useful in stabilizing and preventing damage to stem cells or other cells derived from adipose tissue. In certain embodiments, the inventive system is useful in the transplantation of adult stem cells. In certain embodiments, the inventive system is useful in the transplantation of fibroblasts. Other cells found in adipose tissue include, but are not limited to, stromal cells, smooth muscle cells, blood cells (e.g., macrophages), epithelial cells, and endothelial cells. The invention provides for the transplantation of any such cells.

Kits

The invention also provides packages or kits, comprising one or more polymers or polymer components as described herein in a container. For example, the container may include a polymer or composition of a polymer ready for use in fat transplantation. The package can also include a notice associated with the container, typically in a form prescribed by a government agency regulating the manufacture, use, or sale of medical devices and/or pharmaceuticals, whereby the notice is reflective of approval by the agency of the compositions, for human or veterinary administration in tissue transplantation. Instructions for the use of the polymer may also be included. Such instructions may include information relating to administration of the polymer or a polymer/cell composition to a patient. In particular, the instructions may include information regarding the contacting of the polymer with cells or tissue and administration of the cell/polymer composition to a patient. The package may also include one or more containers containing biologically active agent(s) to be included in the polymer/cell composition prior to administration.

The package may include a device or receptacle for preparation of the polymer/cell composition. The device may be, e.g., a measuring or mixing device.

The package may also optionally include a device for administering a polymer/cell composition of the invention. Exemplary devices include specialized syringes, needles, and catheters that are compatible with a variety of laryngoscope designs.

The components of the kit may be provided in a single larger container, e.g., a plastic or styrofoam box, in relatively close confinement. Typically, the kit is conveniently packaged for use by a health care professional. In certain embodiments, the components of the kit are sterilely packaged for use in a sterile environment such as an operating room or physician's office.

EXAMPLES

Example 1

Enhanced Fat Protection and Survival in Fat Transplantation via Treatment with Poloxamer P188

Introduction. Autologous fat transplantation is an essential tool in soft tissue reconstruction. Damaged and apoptotic cells, however, are eventually resorbed by the body and provide inconsistent and undesirable results for soft tissue restoration. Poloxamer P188 is an agent that interacts with damaged cell membranes and inserts itself into lipid monolayers. This non-ionic surfactant effectively seals the membrane of damaged cells and has been shown to protect against injury and apoptosis. The ability of poloxamers to interact with lipid membranes has led us to hypothesize that by sealing portions of fat cells damaged during fat harvesting, we can restore and protect the structural integrity of damaged cells and thus improve cell survival. This Example investigates the ability of P188 to effectively restore and protect damaged tissues, improve cell survival, and improve transplantation results.

Methods. Fat was obtained for liposuction aspirate and transplanted into nude mice within an hour of harvest from the operating room. A volume of 0.6 mL of fat was placed subcutaneously in the right dorsum of each mouse. The study included three groups: (1) fat treated with P188 at a concentration of 10 mg/mL; (2) fat treated with dextran at a concentration of 10 mg/mL; and (3) fat treated with normal saline. After a period of 6 weeks, mice were euthanized, and fat implants were harvested. Fat implants were evaluated prior to implantation, and after using weight, volume, live/dead assay, mitochondrial ATP levels, and real time PCR for leptin and PPARγ2 levels.

Figure 5:
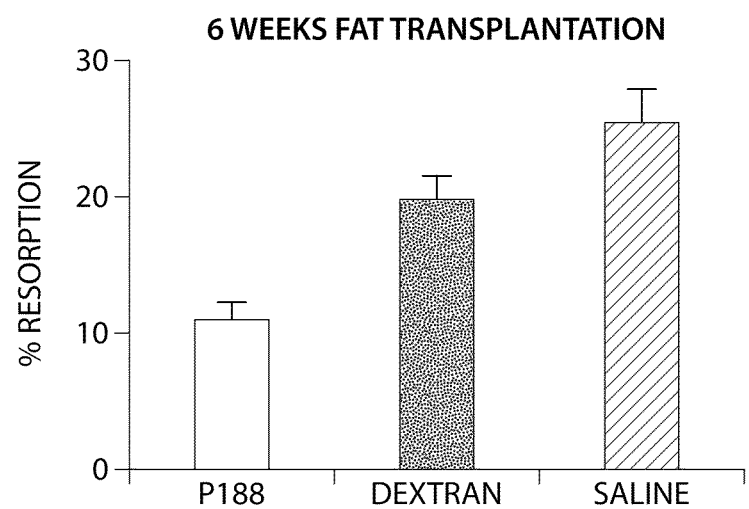
FIG. 5. Resorption of an implantation of 0.6 mL of a composition of cells/poloxymer P188, cells/dextran, or cells/saline after 6 weeks.

Results. Transplanted fat developed into a well circumscribed, demarcated nodule in each animal after a six week period. The saline controls exhibited up to 30% resorption based on weight and volume. Dextran-treated fat grafts exhibited a similar resorption rate. Fat grafts treated with P188 demonstrated a 67% decrease in resorption. See FIG. 5. This is a statistically significant reduction ($p<0.001$). Differences were also seen at the molecular level and histologically with notable increases in proportion of fat cells and decreased vacuolar areas or fibrosis formation.

Conclusion. In this Example, the efficacy and survival of human fat grafts was studied using a nude mouse model of transplantation. Poloxamer P188, a non-ionic surfactant, significantly reduced resorption of fat grafts and improved cell survival. In contrast, treatment with dextran, a comparable molecular weight control, gave results similar to saline. The use of P188 restores and protects fat grafts, improves cell survival, and decreases fat graft resorption.

Example 2

Comparison of P188 with Other Agents for Fat Transplantation

Introduction

Soft tissue injuries and malformations secondary to trauma, congenital defects, infections, and oncologic resections are a source of significant morbidity in patients. At present autologous free flap reconstruction or local advancement flaps are the workhorses of reconstructive modalities for significant soft tissue and bony defects. While, pedicled flaps and free flap reconstructions offer powerful tools for reconstruction, they are not without potentially serious side effects and donor site morbidity. The ability to transfer a large volume of autologous adipose tissue for the reconstruction of these defects would provide a novel reconstructive option for potentially millions of patients, without the associated donor site morbidities. Additionally, it would provide a powerful tool for patients who have poor donor site options, and patients with the inability to tolerate the extended operating times required in flap reconstructions.

The advantage of using lipo-aspirated fat is two-fold: 1) minimal donor site morbidity providing a safe and readily accessible source for autologous cells, and 2) these procedures can be preformed relatively easily without the concern for ischemic complications, and early graft failures associated with vascularized free flaps. However, to date free fat grafts have been plagued with unpredictable high levels of re-absorption and resultant irregularities. Free fat graft failures and volume reduction appear to be related to mechanical stresses from harvesting, early ischemic changes, and nutrient deprivation. These stressors lead to apoptosis. Subsequent, graft re-absorption results from removal of dead cellular debris following re-vascularization.

Thus far, efforts to blunt the initial ischemic insult and protect cells until sufficient vascularity has been established have been met with modest results. Re-absorption presents a significant impediment to long-term fat graft survival, and larger soft tissue wound reconstructive efforts. To this end we have extensively studied membrane stabilization agents including polymers. Some of these polymers have been shown in our laboratory to decrease apoptotic cell death resulting in larger volume fat grafts over time. Mixtures of these polymers may provide a cellular resuscitation solution that will lead to predictable and permanent free fat transplantations.

Figure 1B:
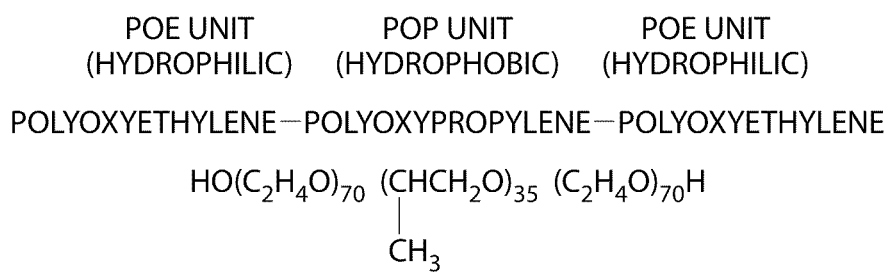

P188 is a tri-block polymer with a central polyoxypropylene hydrophobic region (POP unit, see FIG. 1A) spanning two longer polyoxytheylene hydrophilic tails (POE units, see FIG. 1B). We believe that mechanical trauma and ischemic stress result in a breakdown of the normal adipocyte cellular membrane. This breakdown is first manifested as an increase in porosity and results in the loss of the normal membrane ionic gradient. The loss of membrane electrical integrity is a known potent activator of the apoptotic cascade. Cells that then undergo programmed cell death and remain in the graft as a collection of lipid droplets are then later re-absorbed leading to graft volume loss. Thus, P188 has the ability to insert into traumatized adipocyte membranes, allowing for stabilization of the membrane (see FIG. 2). Additionally, P188 is known to decrease the membrane viscosity with its highly hydrated POE tails. By decreasing cellular viscosity they allow the traumatized cells to become more soluble, thus decreasing the tension on the injured membrane.

It has been demonstrated that the poloxamer P188 is particularly effective for repairing damaged membranes and improving the viability and likelihood of survival of damaged adipocytes. A likely configuration for this repair mechanism is illustrated in FIG. 2. A damaged cell membrane may expose a portion of the central lipid layer to the surroundings. The central hydrophobic portion of a nearby P188 chain may interact with this hydrophobic lipid layer, and the P188 chain may "fold" such that the hydrophilic ends of the chain are located along the outer hydrophilic surface of the cell membrane. This sealing/repair process is analogous to a conventional automotive tire plug repair, where the center of a flexible rubber plug is pushed into a small hole in a tire to seal it, with the ends of the plug being located along the outer tread. A plurality of P188 chains may collect to help seal damaged membranes having different sizes of damaged regions.

Studies have demonstrated this cell membrane salvage process in both electroporation models [Lee et al., *Surfactant-induced sealing of electropermeabilized skeletal muscle membranes in vivo. Proc Natl Acad Sci USA,* 1992. 89(10): 4524-8; incorporated herein by reference] and in ionizing radiation models [Hannig et al., *Surfactant sealing of membranes permeabilized by ionizing radiation. Radiat Res,* 2000. 154(2):171-7; incorporated herein by reference], apart from our own liposuction apoptosis model. Additionally, new studies investigating neuronal injury after blunt trauma have shown that membrane protection with P188 resuscitates cells early in sheer injury by providing mechanical membrane stabilization [Marks et al., *Amphiphilic, tri-block copolymers provide potent membrane-targeted neuroprotection. FASEB J,* 2001. 15(6):1107-9; Serbest, G., J. Horwitz, and K. Barbee, *The effect of poloxamer-188 on neuronal cell recovery from mechanical injury. J Neurotrauma,* 2005. 22(1):119-32; Serbest et al., *Mechanisms of cell death and neuroprotection by poloxamer 188 after mechanical trauma. FASEB J,* 2006. 20(2):308-10; each of which is incorporated herein by reference]. This study, much like ours, demonstrated decreases in apoptosis and increases in cell viability after injury. Interestingly, here again, treated cells appeared more like uninjured, i.e., original neurons, as compared to untreated injured cells.

In this Example, we present the effectiveness of P188 in the rescue of injured adipocytes in the peri-transplant period (the time from harvesting to stable engraftment). Additionally, we demonstrate that polymers closely related to P188 in size and structures have similar effects while not as efficacious as P188.

Methods

Apoptosis Identification. Immunochemistry apoptosis specific fluorescent labels FLIVO™ and MT Mito™ were used to identify apoptosis in adipocytes. Fat grafts were explanted, treated with Blendzyme (Roche Applied Science Liberase Blendzyme 3) at 38° C. for 20 minutes, and passed through a 100 micron cell strainer (to remove extra-cellular stromal elements left behind after digestion). These cells were then incubated for one hour at 38° C., and washed once following labeling. Afterwards these cells were placed into 96 well black plates, and read on a plate reader (Molecular Devices, SpectraMax M2) at their dye-specific emission and excitation wavelengths (FLIVO-red ex 565/em>590, MITO-PT ex 488/em green 530, red 590).

PICO green. Quant-iT PicoGreen® dsDNA Assay Kit from Invitrogen was used for quantification of DNA as a surrogate for cell counts. Each explanted lobule was digested in 1.0 cc of Blendzyme at 38° C. for 30 minutes. Next, the Blendzyme reaction was stopped with 1.0 cc of FBS containing cell-culture media. For quantification 75 microliters of digested fat was removed and processed using a Qiagen Miniprep spin column isolation kit. Extracted DNA samples were then incubated with reagents A (PicoGreen® fluorophore), B (Tris buffer), and for standards with component C (Lambda dsDNA standards, 100 vg/ml concentration), according to kit protocol. These samples were then read on a plate reader, using a black 96 well plate.

Fat Processing. Lipoaspirate was taken directly from the operating room. It was separated into 30 cc aliquots, and washed once with an equal volume of normal saline to remove blood and cellular debris. Afterwards, the tubes were centrifuged at 200G and the middle layer was separated and treated with various agents. These agents were treated in 30 cc washes, with 30 cc of fat for 30 minutes at 37° C. This incubation was chosen to minimize ischemic time while allowing for sufficient mixing with treatment agents. Following incubation and washing, the fat was again centrifuged at 200G. The middle fat layer was again separated and placed in 1.0 cc, 1.0 g aliquots for injection into the flanks of nude mice. This was performed under IRB approval for use of de-identified discarded tissue. Of note, the harvesting cannulas and harvesting pressures varied case by case and surgeon by surgeon. Fat was engrafted into animals within two hours of collection from the operating room in order to minimize warm ischemia time.

Experimental Model. Nude mice were implanted with 1.0 cc/1.0 g (+/−0.01 gm) fat grafts in a single lobule. These mice were injected with a 14 gauge angio-catheter to simulate a clinically relevant 1 cc injection. Two lobules were implanted into bilateral flanks of each nude mouse used in the study. The 14 gauge angio-catheter was chosen to minimize fat graft trauma during injection. Many clinicians use 16 and 14 gauge catheters currently for fat grafting, thus this size catheter was used to approximate clinical practice.

Initially, the lobules were explanted daily and measured for weight and apoptotic activity. After early curves were generated, lobules were explanted on days 3, 6, and 9, for the primary measurement of apoptosis levels. Additionally these samples were weighed, sent for histology, and measured for DNA content. Endpoints in the first ten days were compared to endpoints at six weeks to determine whether graft performance can be accurately predicted by early apoptosis and cell death.

Each experiment consisted of an early group and a late group of mice. Each group was injected with the same fat from a single patient on a single day. For the early time points two animals were euthanized on each sampling day for each group (n=4 lobules per each early time point). Additionally, animals from these same groups were then euthanized at six weeks for examination of late endpoints (8 animals generating 16 lobules were used for each group of late time points). Once an animal was euthanized, both lobules were collected analyzed, and the animal was removed from the study.

Agents tested. For this study a spectrum of various agents were tested. Specifically a variety of polymers were selected to study the effect of different Pluronic subunit chain lengths and configurations.

Pluronics. Pluronics were tested across a range of sizes, different PEG compositions (hydrophilicity), and block configurations. These represent the most widely commercially available poloxamers for non-industrial usage. They were all tested a dose of 50 μM in 25 cc of normal saline. Agents examined were P188 (8,000 KDa/80% PEG content), F38 (4,700 KDa/80% PEG content), F108 (14,600 KDa/80% PEG content), F127 (12,600 KDa/70% PEG content), L64 (2,900 KDa/40% PEG content), T1107 (70% PEG, larger tetra-block poloxamers), and P31R1 (3250 KDa, reversed block order). Also, the di-block (PEG-block-poly-caprolactone-block) was tested.

Non-Pluronic Surfactants

Nonionic. Polysorbate 80 (Tween 80) a polymer with a long hydrophobic tail (oleic acid) and a hydrophilic head (polyethoxylated sorbitan) was tested at the same molar concentration as P188 (50 μM in 25 cc of normal saline). Cholesterol was also tested at the same molarity.

Cationic and Anionic. Hexadecyltrimethylammonium bromide (HCTA, cationic) and cetyltrimethylammonium chloride (CTA, anionic) non-Pluronic charged surfactants were tested at 50 μM in 25 cc of normal saline. These molecules range in the ~360 KDa size and have a short hydrophobic chain with a charged ammonium salt head.

Zwitterionic. Phosphatidylcholine (PC, 790 kDa) a zwitterionic surfactant present in some normal cell membranes was tested. Zwitterionic surfactants can have charged or uncharged properties depending on pH.

Poylethylene glycols (PEG). PEG 8000 was tested at 10 mg/ml since it has the same molecular weight as P188. Additionally PEG 600 and PEG 3350 were tested separately and in combination at 1.3% and 1.5% respectively as was published in literature regarding chondrocyte membrane protection in cyropreservation applications. The number following the PEG represents its molecular weight. PEGs are a component of poloxamers and are entirely hydrophilic.

Additives. Several additives to P188 were tested. Vitamin C was tested at concentrations from 10%-1%, lipoic acid was tested at 500 mM at 100 mg/kg of fat (dose used in rat ischemia-reperfusion models), resveratrol (at 50 μM in 25 cc of normal saline), fructans (organic molecules shown to protect plant membranes undergoing wide temperature variations). Also, cyclosporine (CsA) was examined (a potent immunosuppressive medication).

Statistics. Samples were analyzed using ANOVA or a students T-test for statistical significance between groups. Significance was set at a 95% confidence interval, P<0.05 was considered statistically significant.

Results

Figure 3A:
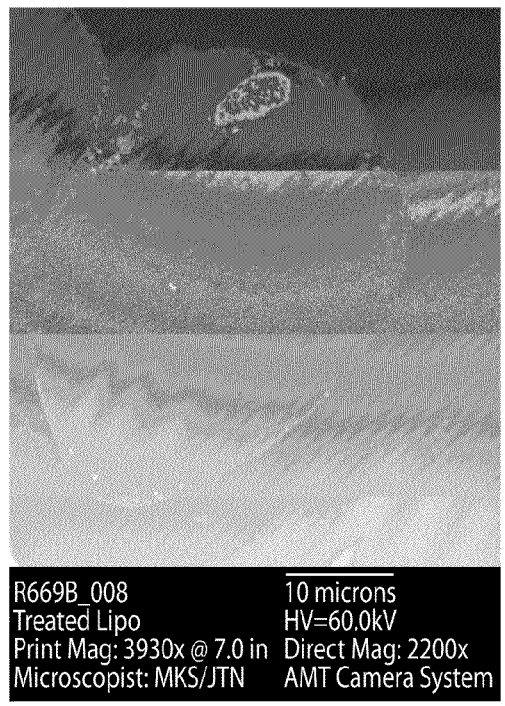
FIG. 3. A. Electron microscopy (EM) of a single intact adipocyte demonstrating an intact lipid bilayer. B. Close-up EM of an adipocyte cell bilayer with membrane pores and sizes noted in nanometers along the membrane surface (arrows).
Figure 3B:
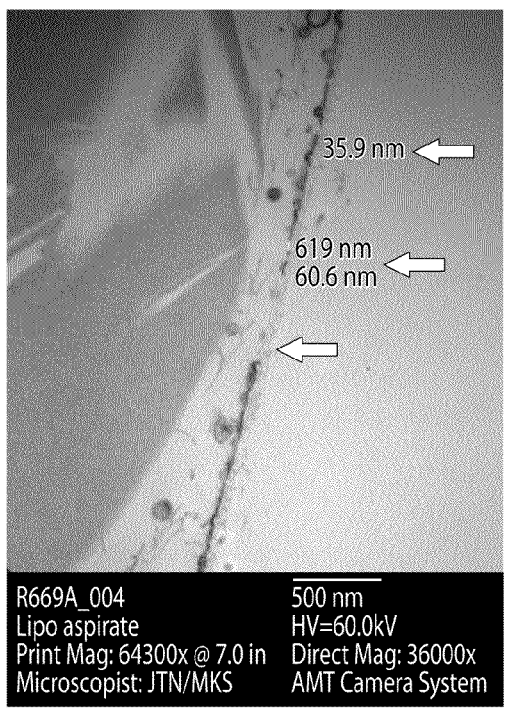
Figure 4:
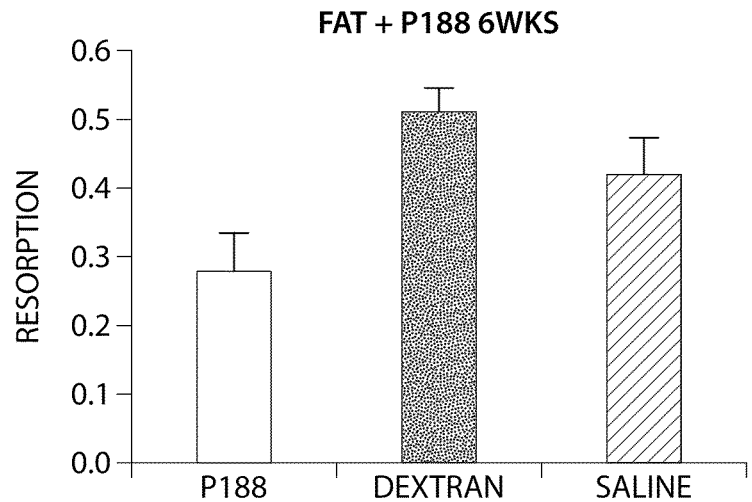
FIG. 4. Resorption of an implantation of 1 mL of a composition of cells/poloxymer P188, cells/dextran, or cells/saline after 6 weeks.

Electron Microscopy. Adipocycles from fresh lipoaspirate were fixed and studied under transmission electron microscopy. These samples were examined for the presence of membrane injury as the result of liposuction harvest. Under electron microscopy we noted pores in the membranes of intact adipocycles immediately following harvesting. These pore were noted to range from 30-600 nm (see FIG. 3). Also, these pores were noted to be in close proximity to the adipocyte mitochondria.

Apoptosis

Figure 6:
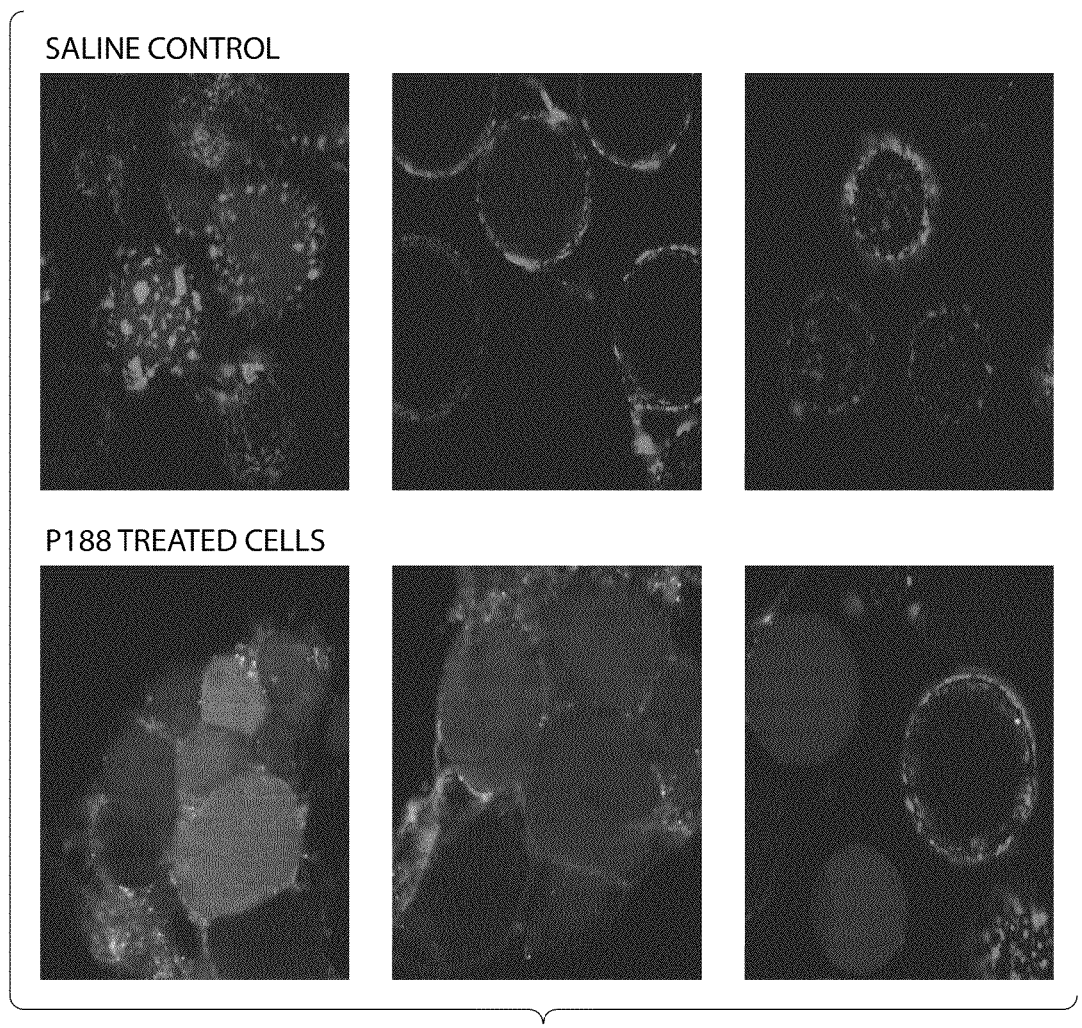
FIG. 6. Day 6 confocal microscopy of saline versus P188 treated fat grafts (1.0 cc, 1.0 g). Cells were labeled using immunochemistry FLIVO-red polycaspase-activated-apoptosis-specific dye. Saline treated controls are shown (top) show large amounts of red labeled apoptotic vesicles. Conversely, day 6 P188-treated samples demonstrate relatively low amounts of red labeled apoptotic vacuoles (green cytoplasm is the result of normal auto-fluorescence).

Confocal Microscopy. Samples from early experiments were explanted for confocal microscopy. These lobules were digested in Blendzyme and labeled with the apoptosis-specific label FLIVO-red; following incubation, these cells were fixed in 4% paraformaldehyde and examined under confocal microscopy for qualitative assessment of apoptosis levels. When adipocytes were visualized using the FLIVO-red SR (excitation 560 nm and 590 nm emission), significant differences between treated and untreated groups were noted (see FIG. 6). Saline-treated samples demonstrated large, red apoptotic vesicles throughout the cell membrane. By contrast, P188 treated samples, at day six, demonstrated relatively few red apoptotic vesicles.

Figure 7:
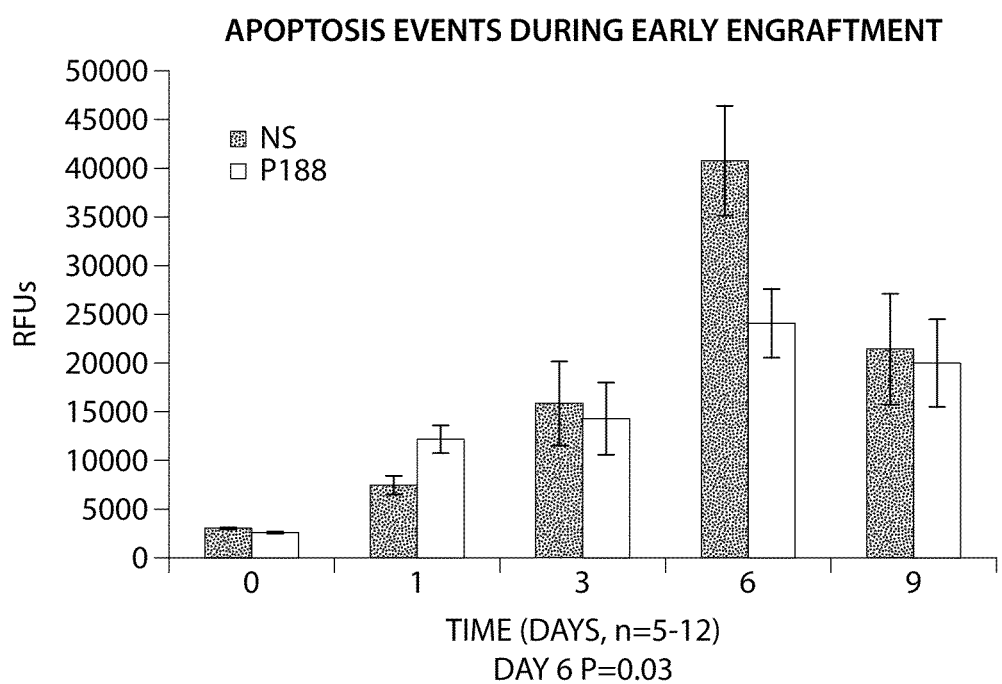
FIG. 7. Apoptosis events during early engraftment. Apoptosis levels in fat grafts during early engraftment. P188 demonstrates statistically significant reductions in apoptotic events on day 6 when compared to normal saline treated controls.

Apoptosis Quantification. Initially, lobules were explanted daily and measured for levels of apoptosis using Mito-PT. After daily testing, it was noted that peak levels of apoptosis occurred between days 5-7, and then trended back down. These values fell approximately in a bell shaped curve. Once this curve was determined, subsequent samples were tested on days 0, 3, 6, and 9, for a sampling of early apoptosis (see FIG. 7).

When P188 was compared to saline treated controls using apoptosis specific labels a statistically significant reduction in apoptotic events was noted on day 6. This difference using a student's t-test assuming no difference between samples demonstrated a p-value of 0.03. On Day 6, normal saline (NS) demonstrated 41,000 RFUs versus P188' s 24,000 RFUs (standard error of the mean+/−5,720 RFUs NS, 4485 RFUs P188). This represents a 40% reduction in apoptotic events on average in P188-treated fat grafts when compared to normal saline-treated controls.

Figure 8:
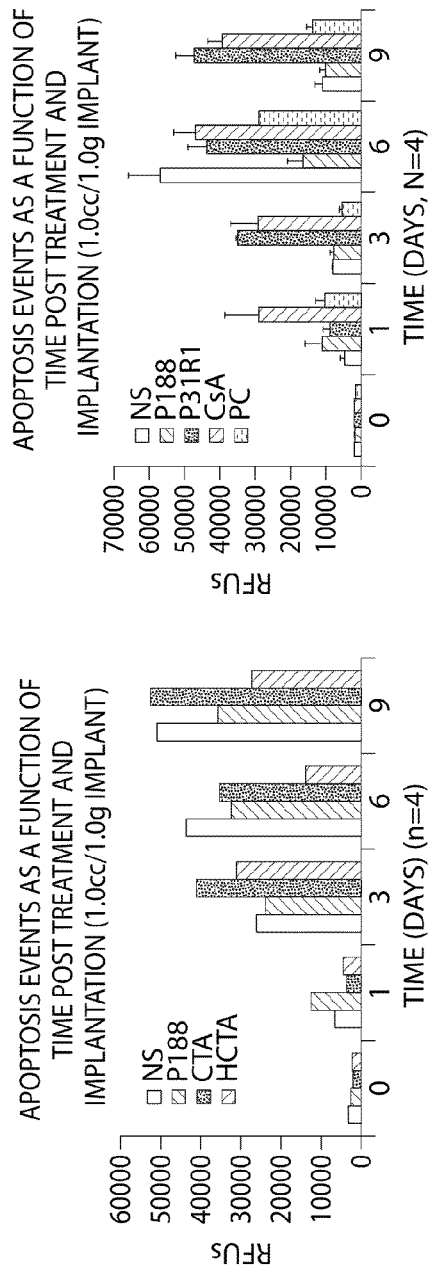
FIG. 8. Increased apoptosis events peri-transplant period with various agents compared to P188. Various polymers and additive agents were compared to P188. The above series demonstrates four separate ten-day experiments where agents performed worse than P188. The agents that increase apoptosis during the early engraftment period are toxic to adipocytes and are not suitable for graft enhancement. (Note: The PEG 8000, T1107 experiment (bottom left) used MitoPT apoptosis labels whereas the other experiments used Promega's Apo-One apoptosis assay. The Apo-One apoptosis assay generates on average a 10-fold higher signal such that the Mito-Pt signals are less bright by our assay method. This is purely an assay difference and does not represent a difference in apoptosis magnitude.)
Figure 8:
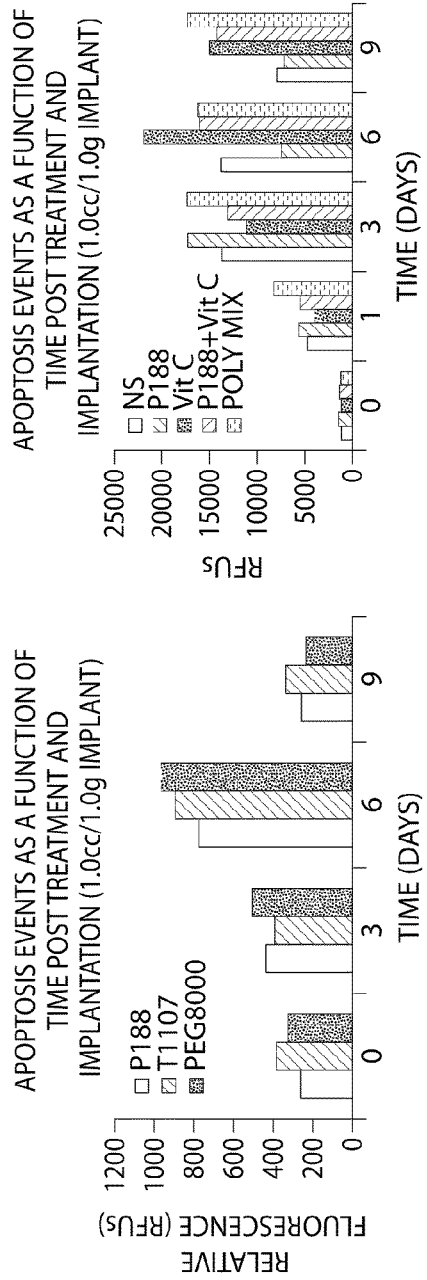
Figure 8:
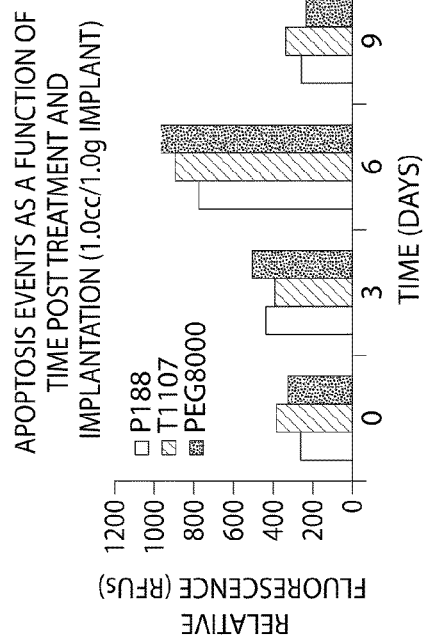

P188 was also compared to several other treatment agents for their impact on apoptosis levels (see FIG. 8). When P188 is compared to anionic and cationic polymers represented by HCTA and CTA, it demonstrated significantly lower levels of apoptosis (Day 6 HCTA 41,037 RFUs, CTA 35,338 RFUs, and P188 32,158 RFUs). Additionally, HCTA and CTA demonstrated higher levels of apoptosis than normal saline controls at earlier time points (Day 3: NS 25,987 RFUs versus HCTA 31,076 RFUs, CTA 35,338 RFUs). These results are consistent with increased early cell death and overall fat graft toxicity with anionic and cationic polymers.

Next, P188 was compared to a reversed triblock copolymer P31R1. This polymer is approximately the same size as P188; however, it is composed of hydrophobic tails and a hydrophilic core (the opposite of P188). When apoptosis levels in P31R1-treated fat were compared to P188- and normal saline-treated controls, P31R1 was also found to increase apoptotic events on days 3, 6, and 9 (Day 3 34,000 RFUs, Day 6 44,000 RFUs, and 47,000 RFUs vs. NS: 8000 RFUs, 57,000 RFUs, and 11,000 RFUs and P188: 8,000 RFUs, 16,000 RFUs, and 10,000 RFUs, respectively). In this same experiment phosphatidylcholine (a non-ionic surfactant phospholipid and component of many cell membranes) was evaluated for its effect on apoptosis. Phosphatidylcholine also demonstrated elevated levels of apoptosis compared to P188. Phosphatidylcholine did not demonstrate increases in apoptosis compared to normal saline (PC Day 3: 52,000 RFUs, Day 6: 2 9,000 RFUs, see FIG. 8, upper right). Of note cyclosporine (CsA), an immunosuppressant, was also tested for apoptotic activity. CsA also failed to decrease apoptosis levels in fat grafts. CsA demonstrated consistently higher levels of apoptosis when compared to normal saline-treated controls on days 1-9. P31R1 and CsA appear to be toxic to fat grafts, and PC may show some reductions in apoptosis when compared to normal saline but not when compared to P188.

P188 was also compared to polyethylene glycol 8000 (PEG 8000) and the tetrablock copolymer T1107. In this series of experiments, an older apoptosis assay method was used (MitoPt vs. Apo-one). The older MitoPT assay method delivers RFU values approximately ten-fold lower than Apo-One. P188 again demonstrated reductions in apoptosis when compared to P188 (see FIG. 8, bottom left). When P188 was compared to combinations of polymers of similar size and configuration, these also failed to further improve apoptosis levels. The combination of P188, F127, and L64 demonstrated higher levels of apoptosis when compared to P188 alone and saline-treated controls. These findings demonstrate early toxicity with PEG 8000, T1107, and the combination of polymers—P188, F127, and L64.

Figure 9:
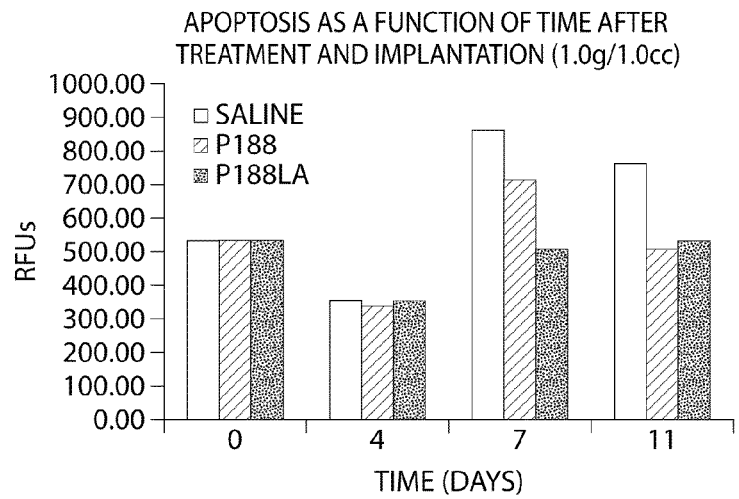
FIG. 9. Lipoic acid has an additive effect in reducing early apoptosis. Lipoic acid treated fat grafts demonstrated decreased apoptosis during the engraftment period when compared to saline treated controls. These improvements in apoptosis lead to improved long term graft performance at six weeks.

Additionally, P188 was studied with lipoic acid and with vitamin C for their effects on apoptosis. P188 combined with vitamin C demonstrated increased apoptosis; however, vitamin C alone also produced high levels of apoptosis (see FIG. 8, bottom left). The combination of P188 and vitamin C demonstrated reduced apoptosis when compared to vitamin C alone. The combination of P188 and lipoic acid demonstrated decreased apoptosis when compared to saline treated-controls (these experiments also used the lower brightness Mito-PT label, see FIG. 9).

Weights

Figure 10:
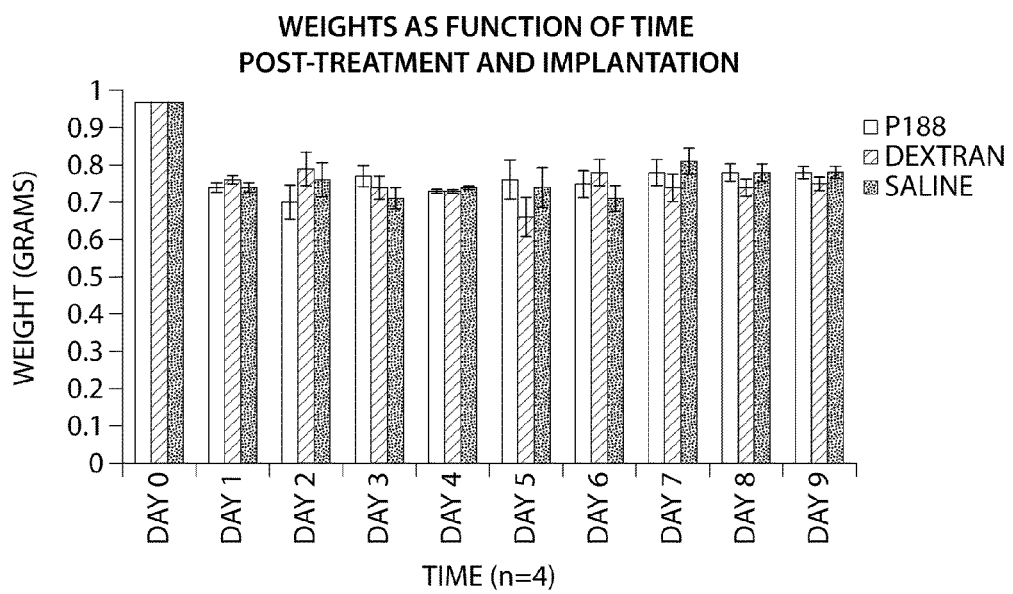
FIG. 10. Weights as a function of time post-treatment and implantation. During the first ten-days following implantation, fat grafts were weighed daily. After the first day, where the graft dehydrates by ~25%, weights during the avascular period were stable between all groups; despite a significant difference in apoptotic activity during the same period. Error bars represent standard deviation which in the early period was ~0.05 g; overall standard deviation in study for weights was ~0.10 g. Dextran was used as an early control since it has a similar molecular weight to P188 and PEG8000. After no differences were demonstrated with dextran, saline was used as the only control group in further experiments.

Early Period. During the first ten days of the experiment, fat lobules were studied for changes in weight. Notable during this period was a 20-25% loss in weight across all groups, immediately after implantation. Our studies yielded an overall 23.6% reabsorption-by-weight in the first 24 hours, with an average weight of 0.75 g (+/−0.8 g). Following this loss in weight on day 1, no significant differences can be identified, and there is little variance in weight between treatment groups in the first ten days (see FIG. 10).

Figure 11:
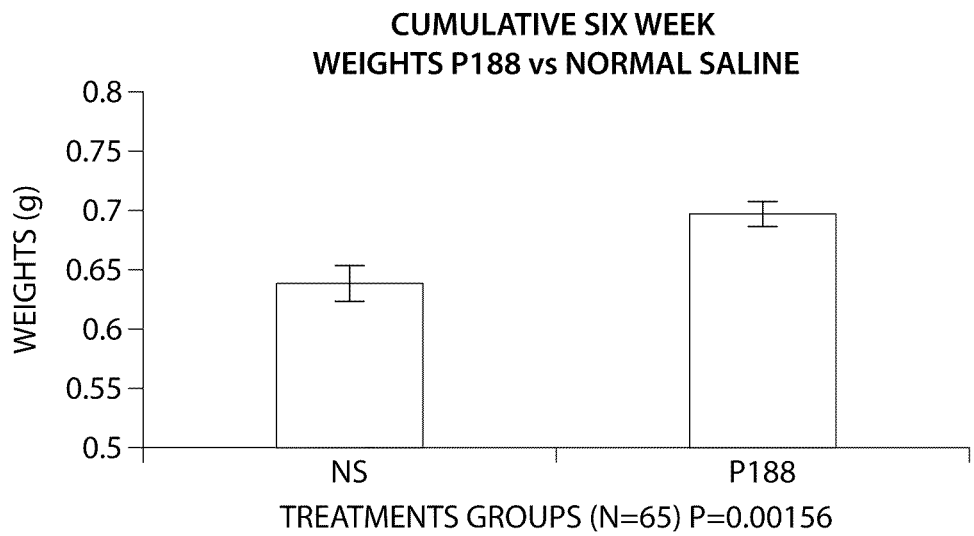
FIG. 11. Cumulative six week weights (P188 vs. normal saline). P188-treated fat grafts demonstrate statistically significant increases in weigh at six weeks when compared to saline-treated controls.
Figure 12:
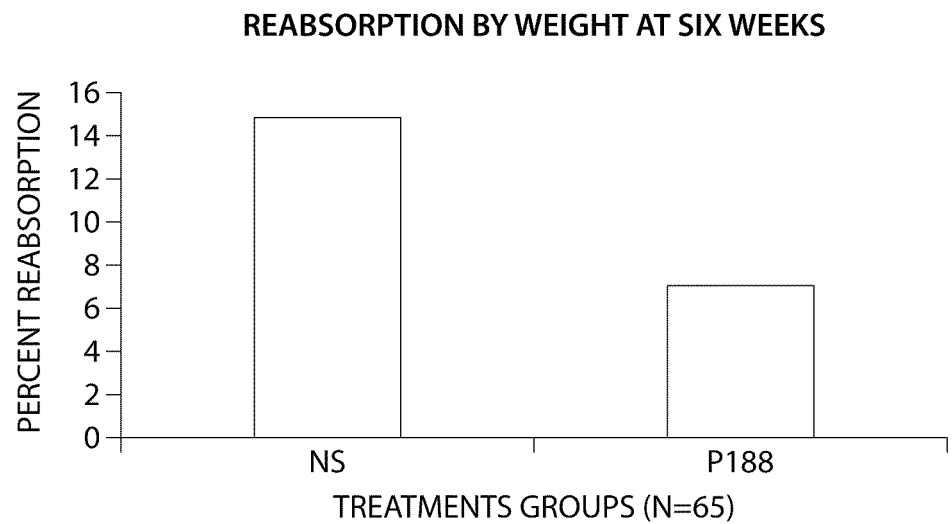
FIG. 12. Reabsorption by weight at six weeks. P188 treatment of fat grafts results in a 50% reduction in graft reabsorption seen at six weeks when compared to saline-treated controls.

P188. P188 when compared to normal saline demonstrated a statistically significant improvement in weight at six weeks. At six weeks with 65 lobules per group analyzed, P188-treated graft demonstrated an average weight of 0.70 g compared to normal saline-treated grafts 0.64 g with standard deviations of 0.08 g and 0.12 g, respectively (see FIG. 11). Further when reabsorption percentages were compared to the dehydrated graft weights at the end of the early sample period P188 demonstrated a 50% reduction in reabsorption when compared to controls (see FIG. 12).

Figure 13:
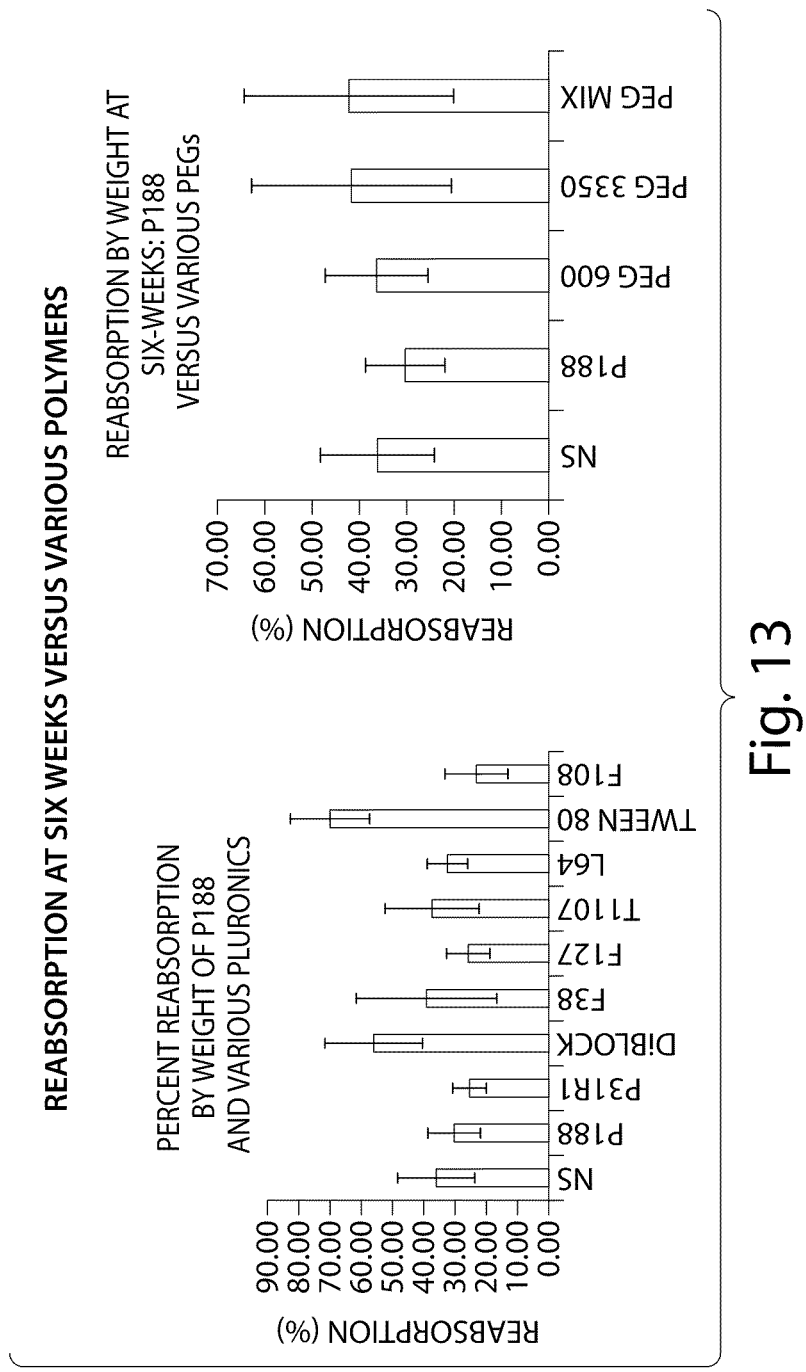
FIG. 13. Reabsorption at six weeks versus various polymers. P188 was measured against a range of different sized Pluronics as well as various sizes and mixtures of PEGs. P188 by weight was among the best performing polymers although by weight alone differences between P188 and some of the other Pluronics was small. Histological specimens of these lobules demonstrate heavy inflammatory infiltrates in some samples and heavy fibrosis in other samples. Thus, weight alone is no a clear indicator of improved fat graft performance.

Other Pluronic Polymers. When compared to other Pluronics, the weights at six weeks were as follows: F127, 0.74+/−0.07 g; L64, 0.68+/−0.06 g; F38, 0.61+/−0.22 g; F108, 0.76+/−0.10 g; T1107, 0.62+/−0.15 g; P31R1, 0.74+/−0.05 g; Diblock, 0.44+/−0.16 g; Tween 80, 0.30+/−0.12 g. The reabsorption percentages are shown on FIG. 13.

Polyethylene glycols. P188 demonstrated statistically significant improvements in weight when compared to PEG 600, PEG 3350, PEG 8000, and PEG 600+3350. PEG 600-treated samples weighed at six weeks on average 0.64+/−0.11 g (normal saline was 0.64+/−0.12 g), PEG 3350 weighed 0.58+/−0.21 g, PEG 8000 0.53+/−0.06 g, and the mixture of PEG 600+3350 weighed 0.58+/−0.22 g. The reabsorption percentages are shown on FIG. 13.

Figure 19:
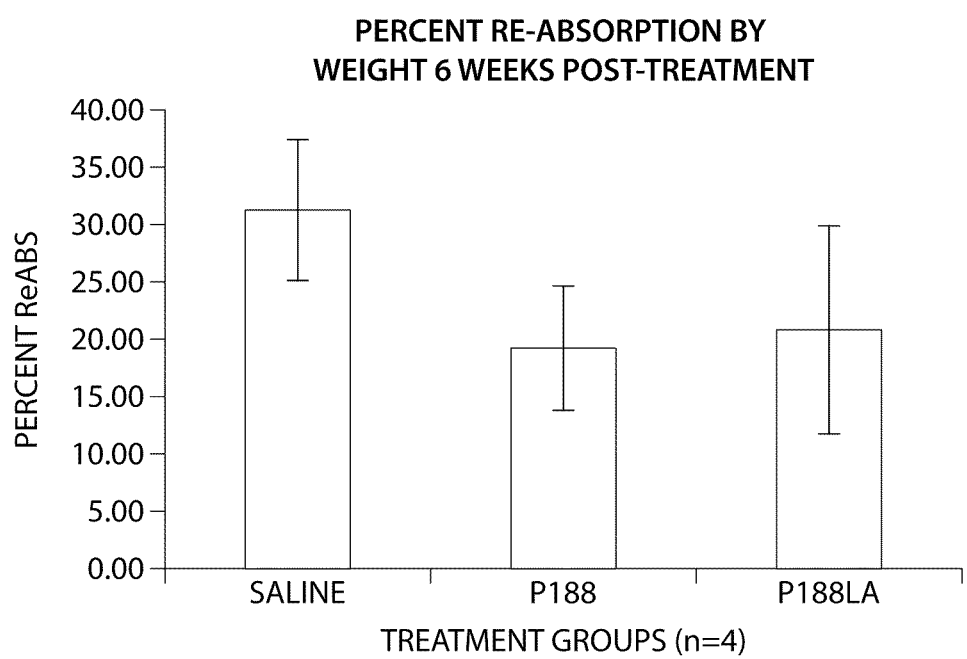
FIG. 19. Percent reabsorption by weight 6 weeks post-treatment.

Lipoic acid. The average ten day weights in this study were normal saline 0.76 g+/−0.09 g; P188 0.76 g+/−0.09 g; and lipoic acid 0.72 g+/−0.09 g (1.0 g+/−0.10 g initial implant). Treatment groups were then reexamined at 6 weeks; here significant differences were noted in the weights. The average weights per group at six weeks were normal saline 0.58+/−0.07 g; P188 0.71+/−0.06 g; lipoic acid 0.65+/−0.09 g; and P188+LA 0.61+/−0.16 g. In comparing early to late changes, re-absorption percentages were calculated using the dehydrated weight of the samples over the first ten days, to six week final weight. P188 and lipoic acid demonstrated statistically significant differences in reabsorption (p-value<0.05), as compared to saline (see FIG. 19).

Miscellaneous Additives. When other agents were tested for potential additive effects with P188, the weights at six weeks were as follows: resveratrol, 0.73+/−0.03 g; cholesterol, 0.73+/−0.04 g; inulin, 0.47+/−0.21 g; oligofructosaccharide, 0.72+/−0.08 g (in this group of experiments, saline performed well with an average weight of 0.74+/−0.04 g).

These agents failed to perform better than saline controls in the experiment and by histology (see below) were found to be mostly toxic.

Cell Viability

Figure 14:
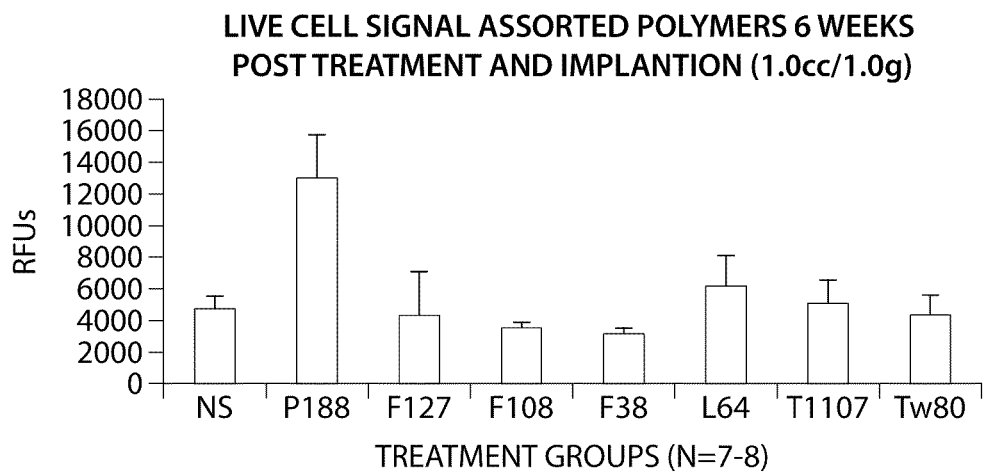
FIG. 14. Live cell signal using various polymers 6 weeks post treatment and implantation (1.0 cc/1.0 g). P188 demonstrates superior live cell signal compared to other Pluronics at six weeks with Cell-Titer Blue viability assay. F127 and L64 demonstrated viability levels at or above normal saline without reaching statistical significance.

Samples harvested at six weeks were assayed with Cell-Titer Blue, which is a blue dye that is concentrated and converted into a dye that fluoresces red in live, metabolically active cells. Conversion of the dye demonstrates metabolic activity and related to cell number in a sample. When P188 was compared to other Pluronics of varying chain length after six weeks, it demonstrated a statistically significant increase in signal (see FIG. 14). P188 demonstrated 12,971+/−2785 RFUs, whereas normal saline controls demonstrated 4727+/−768 RFUs. The remaining polymers were as follows: F127, 4301+/−2785 RFUs; F108, 3529+/−373 RFUs; F38, 3188+/−346 RFUs; L64, 6137+/−1933 RFUs; T1107, 5063+/−1496 RFUs; Tween 80, 4346+/−1231 RFUs. A diblock copolymer (polyethylene glycol methyl ether block poly-caprolactone) and reverse triblock Pluronic (P31R1) were also assayed. These polymers were also inferior to P188: di-block, 1,666+/−1283 RFUs; P31R1, 1453+/−703 RFUs.

Figure 15:
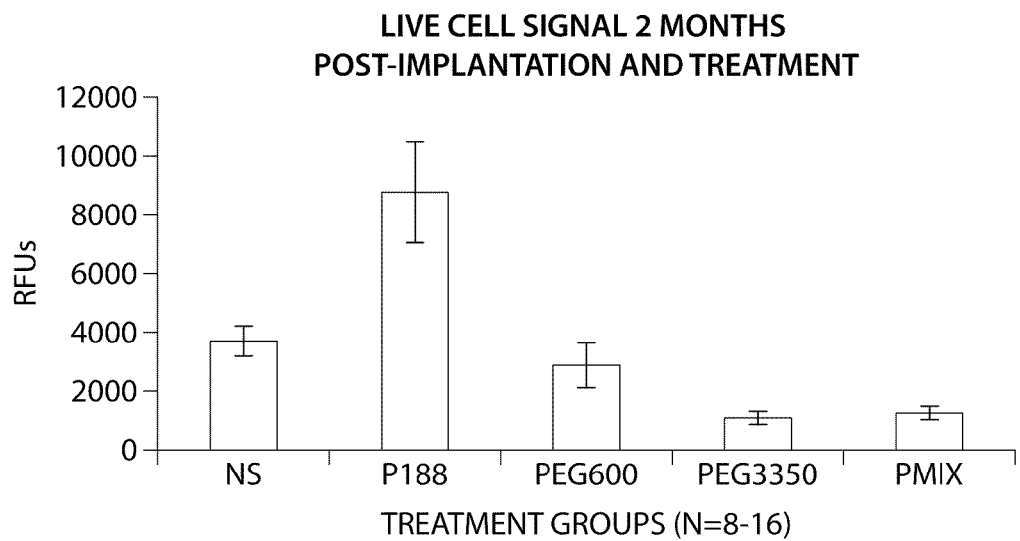
FIG. 15. Live cell signal two months post-implantation and treatment. P188 demonstrates superior cell viability when compared to PEGs across various sizes and in combination after two months post-treatment and implantation. Of note, PEGs demonstrated lower levels of cell viability when compared to saline-treated controls.

P188 was further compared with various sized polyethylene glycols (PEG), which have been shown to protect chondrocytes in other studies, for cell viability in our model. At six weeks, P188 again demonstrated superior cell viability (see FIG. 15). PEGs demonstrated the following cell viability signals: PEG 600, 2892+/−1110 RFUs; PEG 3350, 1109+/−301 RFUs; PEG 600+3350, 1291+/−289 RFUs (see FIG. 15).

DNA Content

Explanted samples were assayed for DNA content, as an indirect measure of cell count. Digested samples were studied at both the early and late time points. Just like the weight measurements, there were no significant difference in DNA content between the samples in the first 10 days.

P188 versus Saline Controls. When P188 was compared to saline controls for DNA content at six weeks the results were as follows: saline controls, 0.129+/−0.052 μg DNA; P188, 0.320+/−0.060 μg DNA. These results were statistically significant with a student's t-test P=0.03.

Pluronics. When P188 was then compared to other Pluronics, a statistically significant difference between P188 and the other polymers was noted (ANOVA analysis p=0.0004, Fcritical=2.299). The DNA content were as follows: F127, 0.236+/−0.043 μg DNA; F108, 0.082+/−0.033 μg DNA; F38, 0.025+/−0.007 μg DNA; L64, 0.168+/−0.062 mcg DNA; T1107, 0.124+/−0.048 μg DNA; Tween 80, 0.134+/−0.023 μg DNA.

PEGs. When PEGs were examined for DNA content, PEG 8000 demonstrated 0.280+/−0.024 μg DNA. PEG 600, PEG 3350, and PEG 600+3350 were also examined.

Histology

Explanted fat lobules were fixed and stained with H&E for scoring of adipose architecture. A statistically significant improvement in normal fat content was noted in P188-treated samples compared to saline-treated controls. P188 when scored for normal fat, inflammatory infiltrate, and fibrosis scored: 58% normal fat, 30% infiltrate, and 13% fibrosis on average (10 lobules, 2 slides per lobule). Normal saline controls scored: 41% normal fat, 38% infiltrate, and 21% fibrosis on average (10 lobules, 2 slides per lobule). P=0.04 when a students t-test was performed.

Figure 18:
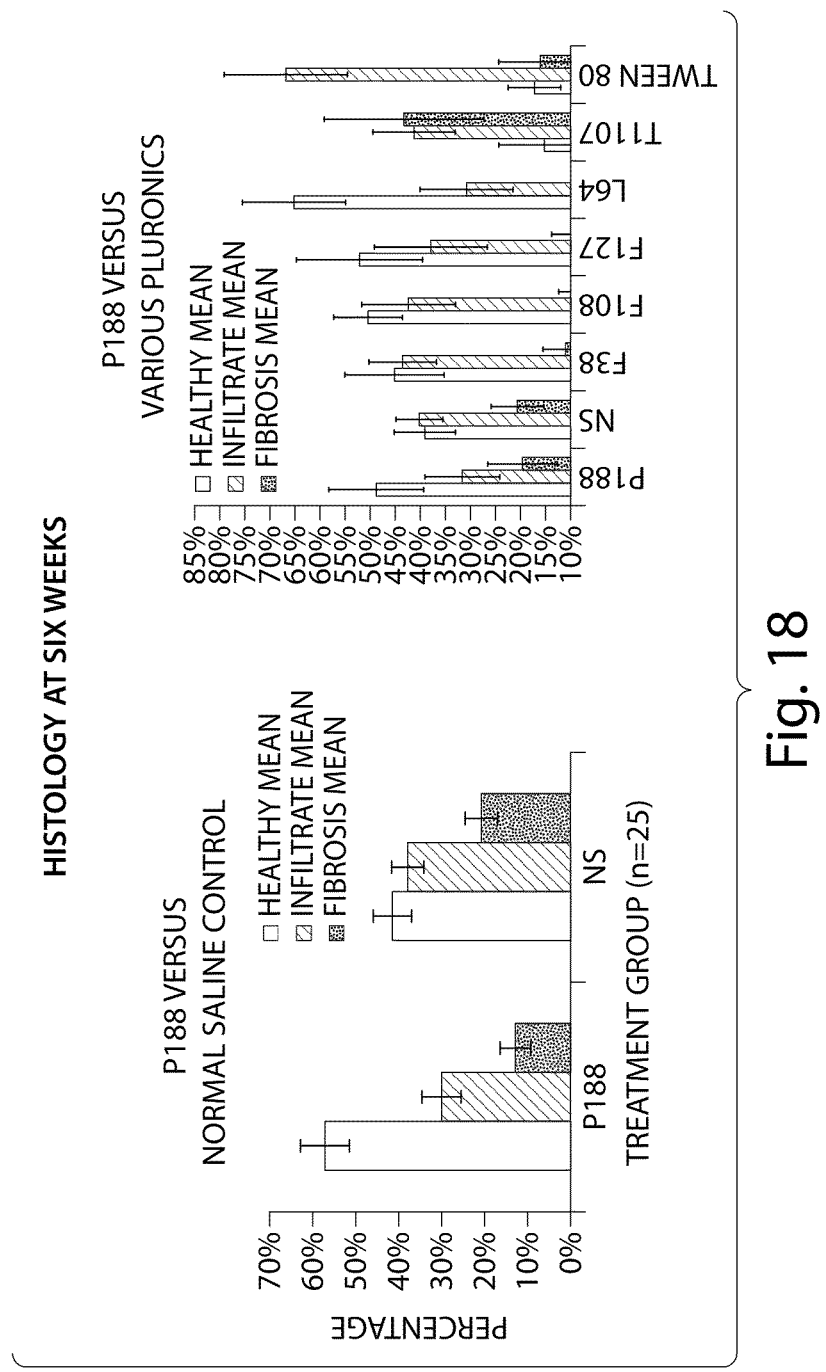
FIG. 18. Histology scoring at six weeks for saline control, P188, and other Pluronics. Samples were scored in a blinded fashion by four examiners for the presence of normal fat, inflammatory infiltrate, and fibrosis. On the left, P188 is compared to normal saline controls. A statistically significant increase in normal fat content was demonstrated as well as a decrease in fibrosis. When compared to other polymers, L64 and F127 scored similarly without statistically significant differences, and the remaining ranged from some improvements over saline to overt toxicity.

Other Pluronics. Of the other poloxamers, L64 and F127 scored the best: L64, 65% normal fat, 31% infiltrate, and 4% fibrosis; F127, 52% normal fat, 38% infiltrate, and 10% fibrosis. These differences did not reach statistical significance when compared to P188. The remaining poloxamers scored as follows: F38, 45% normal fat, 44% infiltrate, 11% fibrosis; F108, 50% normal fat, 42% infiltrate, 7% fibrosis; T1107, 15% normal fat, 41% infiltrate, 43% fibrosis; Tween 80, 17% normal fat, 67% infiltrate, 16% fibrosis (see FIG. 18, right).

Polyethylene Glycols. Fat grafts treated with PEG demonstrated high levels of inflammatory infiltrates and disrupted adipose architecture. PEG 8000 scored: 42% normal fat, 45% infiltrate, 14% fibrosis.

Lipoic Acid. P188 plus lipoic acid (PLA) was also examined and scored. PLA scored: 90% normal fat, 9% infiltrate, 1% fibrosis (n=2).

Miscellaneous Additives. All the remaining additives examined demonstrated toxicity with heavy fibrosis and inflammatory infiltrates.

Discussion

P188, a triblock copolymer with a central polyoxypropylene hydrophobic region (POP unit, see FIG. 1) spanning two longer polyoxyetheylene hydrophilic tails (POE units). We believe that mechanical trauma and ischemic stress result in a breakdown of the normal adipocyte cellular membrane. This breakdown is first manifested as an increase in porosity and results in the loss of the normal membrane ionic gradient. The loss of membrane electrical integrity is a known potent activator of the apoptotic cascade. Cells that undergo programmed cell death remain in the graft as a collection of lipid droplets. These droplets are then later re-absorbed leading to graft volume loss. Triblock copolymers have the ability to insert themselves into traumatized adipocyte membranes, allowing for the stabilization of the membrane. Additionally, triblock copolymers are known to decrease the membrane viscosity with their hydrated POE tails. By decreasing cellular viscosity, they allow the traumatized cells to become more soluble thus, decreasing the tension on the injured membrane.

It has been shown that P188 is poorly soluble in adipose and is not absorbed well onto intact, uninjured membranes. P188 allows adipocytes that have suffered mechanical sheer injury from the harvesting process to maintain their normal membrane mechanics. Once these cells are able to repair their membranes, by increasing the amount of phospholipids in the bilayer, P188 is mechanically extruded [Agarwal, J., A. Walsh, and R. C. Lee, *Multimodal strategies for resuscitating injured cells*. Ann N Y Acad Sci, 2005. 1066:295-309]. The extrusion of P188 is caused by the increase in trans-membrane surface pressure. Also, it should be noted that, it appears that P188 is then excreted essentially unchanged by the kidneys, with a small amount excreted through the biliary enteric system. P188 at these doses we believe there is no evidence for an adverse effect or safety concerns with use in humans [Singh-Joy, S. D. and V. C. McLain, Safety assessment of poloxamers 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and 407, poloxamer 105 benzoate, and poloxamer 182 dibenzoate as used in cosmetics. Int. J. Toxicol., 2008. 27 Suppl 2:93-128].

Additionally, in toxicology analyses preformed to evaluate P188 safety, doses of up to 50 mg/kg were administered IV to dogs and their organs were analyzed for P188 [Singh-Joy, S. D. and V. C. McLain, Safety assessment of poloxamers 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and 407, poloxamer 105 benzoate, and poloxamer 182 dibenzoate as used in cosmetics. Int J Toxicol, 2008. 27 Suppl 2:93-128]. In these experiments, it appears that P188 is not soluble in adipose tissue and almost no radio-labeled P188 was noted in adipose tissue. This further supports the proposed mechanism of action, whereby, P188 is absorbed onto the injured adipocyte membrane without entering adipocytes. Furthermore, there are numerous studies that demonstrate that P188 is extruded from cell membranes once those cell membranes self-seal and the surface pressure increases [Wu et al., Interaction between lipid monolayers and poloxamer 188: an X-ray reflectivity and diffraction study. Biophys J, 2005. 89(5):3159-73; Zhang, Z., M. al-Rubeai, and C. R. Thomas, Effect of Pluronic F-68 on the mechanical properties of mammalian cells. Enzyme Microb Technol, 1992. 14(12):980-3; Maskarinec et al., Direct observation of poloxamer 188 insertion into lipid monolayers. Biophys J, 2002. 82(3):1453-9; Agarwal, J., A. Walsh, and R. C. Lee, Multimodal strategies for resuscitating injured cells. Ann N Y Acad Sci, 2005. 1066:295-309; each of which is incorporated herein by reference].

This ability to prevent ion loss and prevent injured cells from progressing to apoptosis allows adipocytes to retain their ability to act as a soft tissue filler. Without stabilization of the cellular membrane, these cells leak ions and ultimately die [Hannig et al., Surfactant sealing of membranes permeabilized by ionizing radiation. Radiat Res, 2000. 154(2):171-7; Serbest et al., Mechanisms of cell death and neuroprotection by poloxamer 188 after mechanical trauma. *FASEB J,* 2006. 20(2):308-10; Mina et al., Poloxamer 188 copolymer membrane sealant rescues toxicity of amyloid oligomers in vitro. *J Mol Biol,* 2009. 391(3):577-85; each of which is incorporated herein by reference]. Consequently, fat grafts are reabsorbed at unpredictable rates. This unpredictability inherent in free fat grafting decreases the utility of fat grafts for soft tissue reconstruction and augmentation [Coleman, *Structural fat grafts: the ideal filler? Clin Plast Surg,* 2001. 28(1):111-9; Gutowski, Current applications and safety of autologous fat grafts: a report of the ASPS fat graft task force. *Plast Reconstr Surg,* 2009. 124(1):272-80; each of which is incorporated herein by reference].

P188-treated fat grafts appear like normal non-transplanted fat when compared to other fat graft groups. This is best evidenced by histology at six weeks where P188-treated adipose tissue appears the most like native fat (in addition to demonstrating high cell viability by Cell-Titer Blue and thiazolyl blue tetrazolium bromide (MTT)). Saline-treated adipose tissue appears injured as evidenced by large amounts of fibrosis. PEGs (a component of P188 and shown effective by others to protect certain cell types) and tetrablock copolymers (similar to P188 with an extra hydrophilic tail) lead to an inflammatory infiltrate with high to moderate levels of fibrosis.

Figure 17:
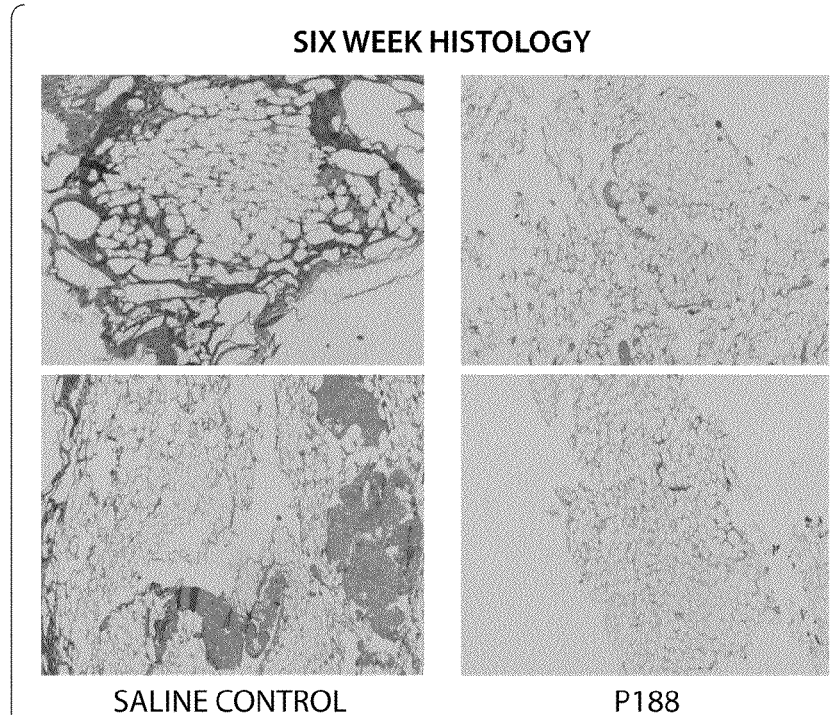
FIG. 17. Six week histology for saline-treated control and P188-treated fat grafts.

The ability to mechanically preserve fat cells during the peri-transplant period results in fat grafts that appear by histological and biochemical analysis like normal fat. Control untreated fat grafts, on the other hand, become fibrotic and loose their normal adipose architecture (see FIG. 17). In similar studies performed with neurons, it was demonstrated that after cells are injured mechanically; P188-treated cells behaved more like uninjured neurons [Marks et al., *Amphiphilic, tri-block copolymers provide potent membrane-targeted neuroprotection. FASEB J,* 2001. 15(6):1107-9; Serbest, G., J. Horwitz, and K. Barbee, *The effect of poloxamer-188 on neuronal cell recovery from mechanical injury.* J Neurotrauma, 2005. 22(1):119-32; each of which is incorporated herein by reference]. Essentially, mechanical membrane stabilization resulted in preservation of neuronal signaling and axon function but did not result in physiologic changes to the cell's normal function.

As evidenced by our data P188-treated fat grafts retain more of their initial weight, cellular function (as assessed by metabolic activity, ATP levels, etc.), and normal architecture than saline-washed cells. This demonstrates preservation of cells during transplant, allowing them to function as normal adipocytes in a new location. Specifically P188 when compared to normal saline-treated controls demonstrates a statistically significant increase in weight at six weeks, which, correlates to a 50% reduction in reabsorption (n=170, P=0.03). Additionally P188 demonstrates a statistically significant decrease in apoptotic events in the first ten days, a significant increase in cell viability at six weeks, a significant increase in DNA content at six weeks, and statistically significant increases in normal fat by histology at six weeks.

Figure 16:
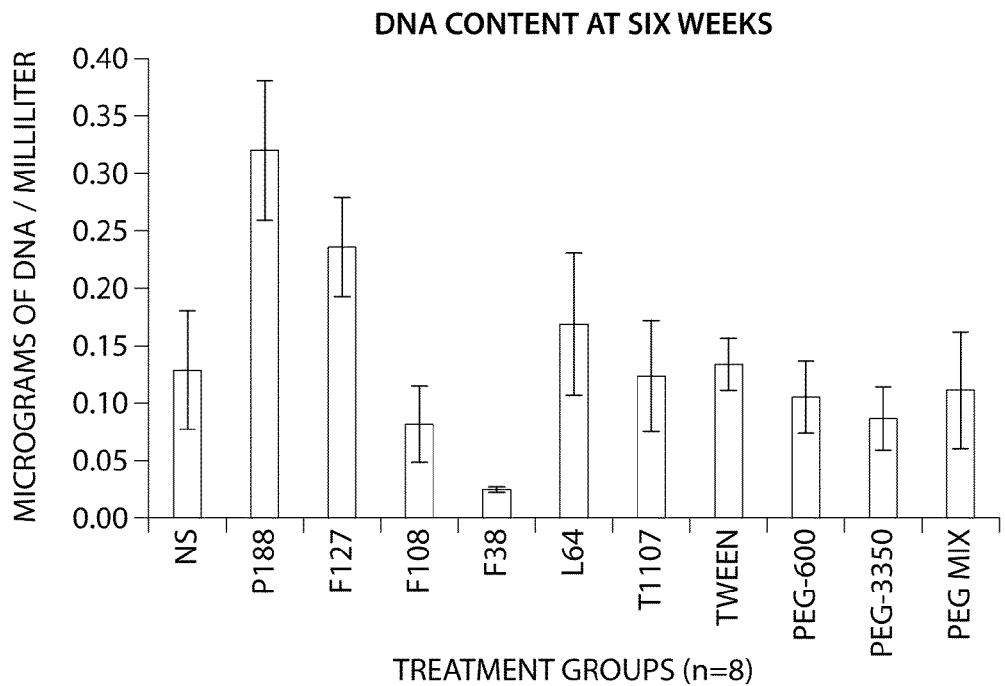
FIG. 16. DNA content at six weeks post-implantation and treatment (1.0 cc/1.0 g). DNA content at six weeks was measured and compared. High DNA content is associated with higher cell counts and more adipocytes. P188 at six weeks demonstrated the highest levels of DNA when compared to other Pluronics. Despite small differences in some of the weights seen at six weeks P188 in terms of DNA content outperformed all other polymers tested.

When P188 is compared to other Pluronics, it also demonstrates superior results. Two other polymers investigated in this study performed similar to P188 but overall remained inferior to P188. These polymers were L64 and F127. L64 is a liquid at room temperature with a molecular weight of 2900 kDa that is 40% PEG and 60% POE. F127 is P407, such that F127 is 12600 kDa with 70% PEG content. These two agents both demonstrated similar reabsorption profiles to P188 (see FIG. 13), along with improved cell viability (L64 versus saline, see FIG. 14, F127 trended higher saline but on average was similar to control) that was not statistically significant when compared to saline controls. Additionally L64 and F127 demonstrated some improvement in DNA content when compared to saline controls (approached but not significant at current n-value) but remained inferior to P188 treated samples (see FIG. 16). These agents when examined histologically, scored for the presence of normal fat, fibrosis, and infiltrate, approached P188 performance. However, since the demonstrated lower cell viability and lower DNA content these grafts remained inferior to P188. These grafts have an overall lower adipocyte cell count although they are relatively healthy by histology and have similar weights to P188.

These polymers demonstrate the size range and effect of different triblock copolymers on membrane sealing properties. L64 is smaller (2900 kDa) and more hydrophobic; F127 is larger (13,000 kDa) and more hydrophilic. P188 is in the middle of these two agents with a ~8000 kDa weight and 80% PEG content. Thus it has longer hydrophilic tails than F127 and a slightly shorter hydrophobic region. L64 is a lighter molecule with shorter PEG chains. The hydrophobic region is critical to membrane sealant activity at the exposed hydrophobic region in the membrane pore. However, it is likely that once the molecule is positioned in the exposed pore that the hydrophilic chains provide additional protection. These chains aid in reducing membrane tension by increasing surface solubility (see FIG. 2).

When P188 was compared to poloxamers F38 and F108 (P98 and P308) these agents demonstrated greater reabsorption, decreased cell viability, and decreased DNA content. While both these agents are 80% PEG, their sizes are very different. F38 is half the weight of P188 while maintaining the same PEG content. This maintains the ratio of hydrophobicity to hydrophilicity, such that F38 is smaller but has the same PEG (hydrophilic) content as P188. F108 is ~15,000 kDa and is therefore larger but also has the same hydrophilic composition. Thus both alterations in chain length effect membrane sealant effects in adipocytes. By histology both these agents induced higher levels of injury than P188 and saline controls. The increase in chain length may lead to greater solubilization of the membrane ultimately causing a detergent effect (cell membrane lysis) with F108 while F38 is likely too small. Although L64 is even smaller, its increased hydrophobic content likely allows it to aggregate in open pores.

This membrane lysis effect seen in higher hydrophilic content poloxamers translates to the results seen with fat grafts treated with pure PEGs. PEG 600, 3350, and 8000 were tested. These PEGs represent a range of PEG weights (e.g., PEG 600=600 kDa polyethylene glycol). In previous studies, mixtures of PEG 600 and 3350 were shown to preserve frozen chondrocytes. U.S. Patent Application Publication US2009/0017438. In our studies adipocytes appear more susceptible to detergent effects than chondrocytes. All the PEG-treated groups (and combinations of PEGs) demonstrated inferior results when compared to P188 and normal saline controls. PEG 3350 and PEG 8000 demonstrated higher reabsorption than saline treated controls (see FIG. 13) and decreased cell viability (see FIG. 15). Additionally by histology this sample demonstrated heavy infiltrates and disrupted adipose architecture. PEG 600 was the least toxic. It demonstrated similar reabsorption by weight to saline controls and similar cell viability (see FIGS. 13 and 15). Consequently PEG 600 is likely too small to have toxic effects at the doses described in chondrocyte protection. The larger PEG 3350 and PEG 8000 lack a hydrophobic region like the triblock copolymers and likely solubilize the cell membrane resulting in cell lysis.

When other co-polymers were analyzed, diblock copolymers, reversed triblock copolymers (e.g., P31R1), and tetrablock copolymers (e.g., T1107), these also demonstrated cellular toxicity (diblock, and reversed triblock) or no effect (tetrablock). The reversed triblock copolymer P31R1 (3,300 kDa) has a central hydrophilic block and two flanking hydrophobic tails. When compared to P188 and normal saline it induces apoptosis throughout most of the peri-transplant period (see FIG. 8, top right). Additionally, it demonstrated lower live signal (1454 RFUs vs. 4,000 RFUs in saline control) and inferior histology despite having a relatively low reabsorption by weight (see FIG. 13). The elevated weight when analyzed by histology represented fibrosis and inflammatory infiltrates with a paucity of normal fat. Thus the configuration of the polymer is important to its membrane sealant properties. Diblock copolymers have the same configuration as soaps; hydrophilic heads with hydrophobic tails. These appear to act as detergents and had among the highest reabsorption levels by weight. The non-ionic non-pluronic Tween 80 also had similar results (see FIG. 13). Tween 80 resulted in the highest levels of injury by histological score and was clearly toxic to fat grafts (see FIG. 18B). The tetrablock copolymer T1107 has four PEG chains attached to four POE chains in a radial fashion (like spokes on a wheel). This polymer performed no better than saline controls by weight, DNA content, and cell viability. However, when T1107 is scored by histology, there is minimal normal fat. Thus the relatively normal appearing viability and DNA content reflect nothing more than inflammatory cells replacing normal fat within the graft. The zwitterionic phosphatidylcholine has been used clinically a fat lysis agent in liposuction. In our ten-day analysis, at the same concentration as P188, it appears to have some protective effect, but not to the same magnitude as P188 (see FIG. 8, top right).

Because L64 and F127 appeared to have some protective effect, they were mixed with P188 and analyzed in the early apoptosis model. We thought perhaps combinations of effective polymers would have a synergistic effect on fat grafts. This was not the case, when combined this mix of polymers appears toxic. High levels of apoptosis were noted throughout the ten-day sampling period (see FIG. 8, bottom right). Thus the mix of polymers was excluded from further study.

Additives to P188 were also investigated. Fructans are plant-derived oligosaccharides that have been shown to protect plant cell membranes from large temperature variations. In our studies however these agents induced large amounts of adipocyte injury (by histology) and high levels of reabsorption by weight. Vitamin C (ascorbic acid) also demonstrated cellular toxicity across a spectrum of doses. Interestingly, in the ten-day model P188 appears to provide some protection to vitamin C treated cells (see FIG. 6 bottom right). Reductions in apoptosis between vitamin C treated samples and vitamin C plus P188 are noted on day 6.

Lastly lipoic acid was also tested as an additive to P188. When lipoic acid is added, there appears to be a synergistic effect on reduction in apoptosis (see FIG. 7). The combination resulted in less apoptotic events on day 6 than P188 alone. Lipoic acid is a potent anti-oxidant, and has mitochondrial protective effects under oxidative stress (ischemia-reperfusion injury). As noted by our electron microscopy the adipocyte mitochondria lay in close proximity to adipocyte membrane pores (see FIG. 3). Thus as the membrane is stabilized by P188, lipoic acid provides additional protection to the injured mitochondria. The mixture also resulted in significantly improved reabsorption by weight and improved DNA content at six weeks.

CONCLUSION

In this Example, we have examined the effects of polymer-based membrane protection on fat grafting. We tested a range of poloxamer sizes (~2500 kDa to ~14,000 kDa), a range of hydrophobicity (40% PEG to 80% PEG), various other co-polymers (diblock, triblock, reversed tri-block, and tetrablock), anionic, cationic, and zwitterionic polymers, plus PEGs alone, in combination, and various additives. In both our early endpoints and late endpoints, P188 has demonstrated superior reductions in apoptosis, improved reabsorption by weight, increased DNA content, and improved cellular architecture when compared to all other groups and saline-treated controls.

It appears that P188's size is an important factor; F38 (smaller) and F108 (larger) do not work as well. Increased hydrophobicity helps smaller poloxamers (L64) and in larger slightly less hydrophic poloxamers (F127); however, P188 still remains superior. Also structure and order are critical, reversed triblock copolymer P31R1 and diblock copolymer PEG-polycaprolactone) are also toxic to grafts. Additionally, the tetrablock copolymer T1107 appears to result in toxicity and heavy inflammatory infiltrates.

When polymers are all hydrophilic and large (PEG 3350, PEG 8000) they are toxic to fat grafts. Small PEGs (PEG 600) are no better than saline. Non-block non-ionic surfactants (Tween 80) also are toxic to fat. High hydrophilicity seen in PEGs likely causes lysis of the membrane by a detergent effect. Tween 80 has a long hydrophobic tail and a smaller hydrophilic head. This molecule also probably acts as a classic detergent and lyses the cell membrane.

The miscellaneous additives were all either toxic or had no effect, except for lipoic acid. Fructans, resveratrol, cholesterol, and vitamin C were all found to be toxic in this study. Interestingly, P188 appears to provide some protection to injury induced by vitamin C. Additionally, lipoic acid appears to provide a potential synergistic effect when used in combination with P188. Thus it would appear that additional mitochondrial protection when may be useful in P188-treated fat grafts.

This study demonstrates P188's effectiveness in sealing adipocyte membrane injury. Molecules that vary too much in size do not appear to work unless their hydrophobicity is increased; however, size continues to be important as these molecules do not work as well as P188, and in combination are likely toxic. Lipoic acid, which works under a completely different mechanism, may have synergistic effect when combined with P188.

Equivalents and Scope

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. For example, it is to be understood that any of the compositions of the invention can be used for soft tissue repair or augmentation. It is also to be understood that any of the compositions made according to the methods for preparing compositions disclosed herein can be used for soft tissue repair or augmentation. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A method of preventing the resorption of a fat graft comprising:
   (a) administering a composition of fat-derived cells and POLOXAMER P188 to a subject, and
   (b) allowing a fat graft derived from the composition to form in the subject,
   wherein the POLOXAMER P188 prevents resorption of the fat graft, protects the cells from injury, and prevents cell death.

2. The method of claim 1, wherein the fat-derived cells are adipocytes.

3. The method of claim 1, wherein the fat-derived cells are stem cells.

4. The method of claim 1, wherein the fat-derived cells are autologous cells.

5. The method of claim 1, wherein the composition of fat-derived cells and POLOXAMER P188 further comprises lipoic acid.

6. The method of claim 1, wherein the composition comprises about 1 mg to about 20 mg of POLOXAMER P188 per ml of cells.

7. The method of claim 1, wherein the composition comprises about 5 mg to about 15 mg of POLOXAMER P188 per ml of cells.

8. The method of claim 1, wherein the composition comprises about 15 mg of POLOXAMER P188 per ml of cells.

9. The method of claim 1, wherein the composition comprises about 10 mg of POLOXAMER P188 per ml of cells.

10. The method of claim 1, wherein the POLOXAMER P188 is at least 95% pure.

11. The method of claim 1, wherein the POLOXAMER P188 is at least 98% pure.

12. The method of claim 1, wherein the POLOXAMER P188 is at least 99% pure.

13. The method of claim 1, wherein the subject is a mammal.

14. The method of claim 1, wherein the subject is a human.

* * * * *